United States Patent
Ip et al.

(10) Patent No.: US 9,629,863 B2
(45) Date of Patent: Apr. 25, 2017

(54) CDK5 INHIBITORS AND THERAPEUTIC USES THEREOF

(71) Applicant: The Hong Kong University of Science and Technology, Hong Kong (CN)

(72) Inventors: Nancy Yuk-Yu Ip, Hong Kong (CN); Fanny Chui-Fun Ip, Hong Kong (CN); Wing Yu Fu, Hong Kong (CN); Guangmiao Fu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 14/586,443

(22) Filed: Dec. 30, 2014

(65) Prior Publication Data

US 2015/0119348 A1 Apr. 30, 2015

Related U.S. Application Data

(62) Division of application No. 13/513,744, filed as application No. PCT/CN2010/001982 on Dec. 7, 2010, now abandoned.

(60) Provisional application No. 61/282,039, filed on Dec. 7, 2009.

(51) Int. Cl.
| | |
|---|---|
| A61K 31/7048 | (2006.01) |
| A61K 31/353 | (2006.01) |
| A61K 31/352 | (2006.01) |
| A61K 36/41 | (2006.01) |
| A61K 31/19 | (2006.01) |
| A61K 31/7004 | (2006.01) |
| A61K 31/7016 | (2006.01) |
| C07H 15/10 | (2006.01) |
| C07D 311/62 | (2006.01) |

(52) U.S. Cl.
CPC .......... *A61K 31/7048* (2013.01); *A61K 31/19* (2013.01); *A61K 31/352* (2013.01); *A61K 31/353* (2013.01); *A61K 31/7004* (2013.01); *A61K 31/7016* (2013.01); *A61K 36/41* (2013.01); *C07D 311/62* (2013.01); *C07H 15/10* (2013.01)

(58) Field of Classification Search
CPC . A61K 31/7048; A61K 31/353; A61K 31/352
See application file for complete search history.

(56) References Cited

FOREIGN PATENT DOCUMENTS

CN 1534040 A 10/2004

OTHER PUBLICATIONS

Cruz et al., Curr. Opin. Neurobiol., 2004, 14, p. 390-394.*
Definition of prevent, Oxford English Dictionary Online, http://dictionary.oed.com/, accessed online Mar. 27, 2010, especially definition 9a. at p. 2.*
National Institute on Aging, "Preventing Alzheimer's Disease: What Do We Know?", Sep. 2012, U.S. Department of Health and Human Services, Publication No. 12-5503.*
Platikanov et al., Economic Botany, 2008, 62(4), p. 621-627.*
Cheung et al., Neuron, 2006, 50, p. 13-18.*
Aliotta, G. et al. "Three Biologically Active Phenylpropanoid Glucosides From *Myriophyllum verticillatum*" *Phytochemistry*, 1992, 31(1):109-111.
Zapata-Torres, G. et al. "Effects of Natural Flavones and Flavonols on the Kinase Activity of Cdk5" *Journal of Natural Products*, 2004, 67:416-420.
International Search Report in International Application No. PCT/CN2010/001982, filed Dec. 7, 2010.
Brown, et al., HerbalGram, 2002, 56, p. 40-52.
Mook-Jung et al., Biol. Pharm. Bull, 2002, 25(8), p. 1101-1104.

* cited by examiner

*Primary Examiner* — Jonathan S Lau
(74) *Attorney, Agent, or Firm* — Saliwanchik, Lloyd & Eisenschenk

(57) ABSTRACT

Natural occurring inhibitors of cyclin-dependent protein kinase 5 (Cdk5), isolated from the root of *Rhodiola rosea* are structurally different from the known Cdk inhibitors. They show selectivity among different Cdks and efficacy to inhibit Cdk via a mixed-type of inhibition, which should lead to less toxicity and side-effects. They are useful in preventing and treating diseases and disorders associated with aberrant Cdk5 activities, such as acute and/or chronic pain, neuropathic pain, diabetes mellitus, cancer, neurodegenerative diseases and neuropathological disorders.

12 Claims, 15 Drawing Sheets

| Drug | IC50 (uM) | Maximum inhibition |
|---|---|---|
| F199-C4 (gallic acid) | 40.6 | 64.19% at 200 μM |
| F199-C6 (rodalin) | 34.4 | 56.61% at 200 μM |
| F199-C16 (litvinolin) | 3.24 | 87.5% at 200 μM |
| F199-C22 (6-O-galloyl rosin, novel structure) | 20.1 | 46.5% at 80 μM |
| F199-C23 (4'-methoxyherbacetin) | 1.21 | 45% at 20 μM |
| F199-C34 (6-O-galloyl arbutin) | 5.63 | 70% at 80 μM |
| F199-C35 (epigallocatechin-3-gallate) | 14.72 | 68.4% at 200 μM |

CDK5 INHIBITORS AND THERAPEUTIC USES THEREOF

CROSS-REFERENCE TO RELATED APPLICATIONS

This application is a divisional of U.S. application Ser. No. 13/513,744, filed Jun. 27, 2012, which is the U.S. national stage application of International Patent Application No. PCT/CN2010/001982, filed Dec. 7, 2010, which claims priority to U.S. Provisional Application No. 61/282,039, filed Dec. 7, 2009, which are hereby incorporated by reference in their entirety.

BACKGROUND

Technical Field

This invention relates to new Cdk inhibitors isolated from natural sources for therapeutic uses. More particularly, it relates to compounds that are naturally occurring Cdk5 inhibitors from the plant Rhodiola rosea and their biological activities as Cdk5 inhibitors.

Background of the Invention

With today's high throughput chemical synthetic technologies and high efficiency screening methodologies, it may not be difficult to find chemical compounds that show promising biological effects at the cellular level in the laboratory. However, the rate of these compounds becoming clinically useful is very low due to a number of factors. A key factor is their toxicity and side effects, which are often severe and may not be tolerable by the human body during later stages of drug development. In this respect, new compounds discovered from natural sources that have been used therapeutically for thousands of years have received renewed attention due to the fact that they have been consumed by humans for a long time and thus, their toxicity and side effects are more likely to be more tolerable than purely synthetic compounds.

Cyclin-dependent kinases (Cdks) belong to a family of proline-directed serine/threonine kinases that play important roles in controlling cell cycle progression and transcriptional control. Activation of Cdks requires the association with specific regulatory subunits, cyclin, and requires the phosphorylation at specific threonine residues on Cdks. Cdk1, 2, 3, 4 and 6 play important roles in regulating the transition of different cell cycle phases. Cdk1 is a mitotic Cdk, whereas Cdk2, 4 and 6 are interphase Cdks that play regulatory roles in the progression of quiescent G1 to S phases. Therefore, abnormal activation of Cdks leads to cell cycle deregulation such as continued cell proliferation or unrestrained cell cycle re-entry, and subsequent development of diseases such as cancers (Shapiro, 2006; Malumbres & Barbacid, 2009). Cyclin-dependent kinase 5 (Cdk5), a proline-directed serine/threonine kinase, is unique due to its indispensable role in neuronal development and function. Despite its structural homology with other Cdks, Cdk5 may not be involved in the regulation of cell cycle. Activation of Cdk5 is dependent on its association with two specific activators, p35 and p39, which are expressed in neuronal cells. Therefore, while Cdk5 is expressed ubiquitously in cells, it is mainly active in postmitotic neurons due to the restricted expression of p35 and p39 (Tsai et al., 1993; Zheng et al., 1998).

Cdk5 plays a diverse physiological role in neural cells, including neuronal migration (Xie et al., 2003) and axon guidance (Connell-Crowley et al., 2000) during early neural development as well as synapse formation and synaptic plasticity (Cheung et al., 2006; Lai and Ip, 2009). However, more recently, Cdk5 has also been found to play important roles outside the central nervous system such as pain signaling that involves the sensory pathways (Pareek et al., 2006), and in modulating glucose-stimulated insulin levels in pancreatic beta cells, (Wei et al., 2005). Due to its key physiological roles, uncontrolled activity of Cdk5 has been linked to various diseases/disorders such that Cdk5 has emerged as a potential molecular target for therapeutic drugs. In neurons, Cdk5 deregulation triggers neuronal apoptosis (Cheung and Ip, 2004), suggesting that aberrant regulation of Cdk5 activity is responsible for the progression of neurodegenerative diseases such as Alzheimer's disease (AD) and Parkinson's disease (PD). Aberrant Cdk5 activity, for example, is also linked to cancer development, progression and metastasis such as prostate and thyroid carcinoma (Strock et al., 2006; Lin et al., 2007).

The two major pathological hallmarks of AD are the accumulation of senile plaques and neurofibrillary tangles in the diseased brain. The deregulation of Cdk5 is caused by the presence of p25, a cleavage product of p35 generated under pathological conditions (Patrick et al., 1999). Accumulation of p25 protein is found in the brains of AD patients (Patrick et al., 1999). Recent findings also indicate that Cdk5 is one of the key kinases that regulate the formation of senile plaques (Monaco, 2004) and neurofibrillary tangles (Cruz et al., 2003).

Another major neurodegenerative disease that links to Cdk5 is PD). Pathologically, PD is characterized by motor impairment due to the progressive death of selected populations of neurons, especially the dopaminergic neurons in the substantia nigra pars compacta (Muntane et al., 2008). In a PD mouse model induced by 1-methyl-4-phenyl-1,2,3,6-tetrahydropyridine (MPTP), elevated expression and activity of Cdk5 have been reported to be correlated with dopaminergic neurons cell death (Smith et al., 2003; Qu et al., 2007). Moreover, it is of interest to note that inhibition of Cdk5 results in an increase in dopamine release, which may help ameliorate PD progression (Chergui et al., 2004). Cdk5 has also been implicated in a plethora of other neurodegenerative diseases and neurological disorders such as Huntington's disease (Anne et al., 2007), Amyotrophic Lateral Sclerosis (ALS; Bajaj et al., 1998) and ischemic injury (Wang et al., 2003).

More recently, aberrant Cdk5 activity has been linked to the pathogenesis of diabetes mellitus (type-2 diabetes). p35, the activator of Cdk5, is present in pancreatic beta cells and its activity negatively modulates insulin release in response to glucose (Wei and Tomizawa, 2007). A sustained increase in p35 protein and Cdk5 activity is reported in murine pancreatic beta cells upon high glucose exposure (Ubeda et al., 2006). Moreover, inhibition of Cdk5 activity by chemical inhibitors increases insulin secretion in cultured beta cells and in a mouse model of diabetes in a glucose-dependent manner (Ubeda et al., 2006). These findings are consistent with the observation that p35−/− mice exhibit enhanced insulin secretion upon glucose challenge (Wei et al., 2005). Cdk5 is thought to act through the regulation of the $Ca^{2+}$ channel activity or regulation of insulin gene expression during glucotoxicity (Wei et al., 2005; Ubeda et al., 2006). Thus, Cdk5 inhibitors could be potential therapeutic agents for the treatment of type-2 diabetes (Kitani et al., 2007).

Cdk5 has also been emerging as a major potential target for analgesic drugs. Cdk5/p35 has been indirectly linked to nociceptive pathways. For example Cdk5 regulates the activation of mitogen activated protein kinase (MAPK) in nociceptive neurons potentially modifying the hyperalgesia that results in increased MAPK activity. Cdk5 has also been implicated in other pain pathways such as calcium calmodulin kinase II, delta FosB, the NMDA receptor and the P/Q type voltage-dependent calcium channel. Furthermore, studies suggest that Cdk5 inhibitors may be of benefit in the management of acute pain. Cdk5/p35 is shown to be involved in the processing of pain while its inhibition reduces the responsiveness of normal pain pathways (Pareek et al., 2006; Pareek and Kulkarni, 2006). More specifically, peripheral inflammation in rats induces an increase in Cdk5 activity. While p35 transgenic mice with elevated Cdk5 activity are more sensitive to painful stimuli, p35−/− and conditional Cdk5−/− mice with markedly reduced Cdk5 activity show delayed response to pain stimuli (Pareek et al., 2006; Pareek et al., 2007). Cdk5 also regulates mitogen-activated protein kinase1/2 (MEK1/2)/1M activity through a negative feedback loop during a peripheral inflammatory response (Pareek and Kulkarni, 2006). In addition, transient receptor potential vanilloid 1 (TRPV1), a ligand-gated cation channel that is activated by heat, protons and capsaicin, was recently identified as a substrate of Cdk5 (Pareek et al., 2007). Since phosphorylation of TRPV1 by Cdk5 regulates the functions of TRPV1 during pain signaling, it is believed that Cdk5 could serve as a new molecular target for developing analgesic drugs.

Since Cdk5 is associated with various diseases, screening of inhibitors that target Cdk5 may help identify potential drug leads. However, to date, only a few Cdk5 inhibitors have been identified and they are far from being ready for clinical evaluation for neuro-indications. Roscovitine, a member of the 2,6,9-substituted purine analogs, is one of the Cdk5 inhibitors in development but it also targets Cdk1, Cdk2, Cdk7 and Cdk9 (Meijer et al., 1997). Currently, roscovitine is in phase-2 clinical trials for non-small cell lung carcinoma, breast cancer, and B-cell malignancies. The indirubin family is another class of Cdk inhibitors that has its roots in Chinese medicine. The bis-indole indirubin is an active component of Ganggui Longhui Wan, a traditional Chinese medicine recipe used for the treatment of leukemia and other chronic illnesses due to its antimitotic and antitumor activities (Leclerc et al., 2001). Indirubin inhibits various kinases including Cdk1, Cdk5 as well as glycogen synthase kinase-3 beta (GSK3β). GSK3β, together with Cdk5, is believed to be responsible for the hyperphosphorylation of TAU observed in AD.

Clearly, the scientific literature strongly indicates that Cdk5 inhibitors are promising therapeutic agents for the treatment of pain and in the management of type-2 diabetes, and may also be useful in treating neurodegenerative diseases and neurological disorders. Yet, there is a lack of promising candidate compounds that can effectively inhibit Cdk5 over other Cdks.

SUMMARY OF THE INVENTION

One object of the present invention is to provide a butanol fraction of *Rhodiola rosea* root having excellent Cdk5 inhibitory activity, and a composition comprising the same.

Another object of the present invention, accordingly, is to provide a number of natural occurring compounds showing inhibitory effects on Cdk5 with high specificity. All the compounds are isolated and purified from a natural herb *Rhodiola rosea*. Some of those compounds are novel and have a structure of formula (I):

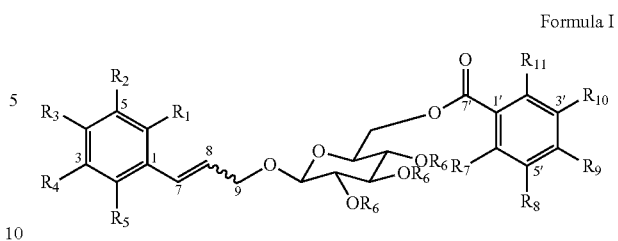

Formula I where $R_1$-$R_{11}$ are each independently unsubstituted (i.e., being hydrogen) or substituted with the same or independently different substituents deemed suitable by a person of ordinary skill in the art. Example is as follows: F199-C22. A "substituent" is a commonly used term in organic chemistry and is understood by a person of ordinary skill in the art to be an atom or group of atoms substituted in place of a hydrogen atom on the parent chain of a hydrocarbon. It is within ordinary skill of the art to know what a particular substituent can be at a given position on the parent chain of hydrocarbon or the backbone without undue experimentation. Thus, for the present invention and the claims thereof, the term "substituent" means a suitable replacement of the hydrogen atom on the parent chain of a hydrocarbon, which is obvious to or easily determined by a person of ordinary skill in organic chemistry without needing undue experimentation. Examples of possible substituent for $R_1$-$R_5$ may be hydroxyl, alkoxyl, acyl, halogen, alkyl, heteroalkyl, arylalkyl, cycloalkyl, cycloalkyl-alkyl, haloalkyl, heterocycloalkyl or aryl. For $R_6$, the substituent may be acyl, alkyl, heteroalkyl, arylalkyl, cycloalkyl, cycloalkyl-alkyl, haloalkyl, heterocycloalkyl or aryl, except Ph-CO. For $R_7$-$R_{11}$, the substituent may be hydroxyl, alkoxyl, acyl, halogen, alkyl, heteroalkyl, arylalkyl, cycloalkyl, cycloalkyl-alkyl, haloalkyl, heterocycloalkyl or aryl. The wavy line denoted by ΛΛΛΛΛ indicates the carbon to which the wavy line is attached has a configuration of cis, trans or a mixture thereof.

Of course, as it is understood by people of ordinary skill in the art, those natural occurring compounds may be produced by synthetic processes in the laboratory or in an industrial scale. It is further understood that those identified compounds may be made in the forms of a pharmaceutically acceptable salt, prodrug, hydrate and isomers thereof as it may be deemed suitable by the users under their particular situations.

Another object of the present invention is to provide a method of inhibiting Cdk5 activities, specifically, inhibiting Cdk5/p25 and Cdk5/p35 activities, with high specificity. The objected is achieved by contacting the enzyme with the compounds isolated from a natural herb *Rhodiola rosea*. Some of the compounds are of formula II or III:

Formula II where $R_1$-$R_7$ are each independently unsubstituted (i.e., being hydrogen) or substituted with the same or independently different substituents deemed suitable by a person of ordinary skill in the art, for example wherein
$R_1$, $R_2$ and $R_3$ are independently H, OH or $OCH_3$;
wherein $R_4$ is OH or $OR_{12}$, wherein $R_{12}$ is glucose,

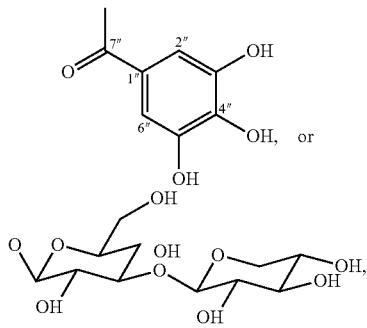

with the proviso that when $R_{12}$ is

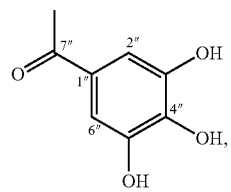

the bond between C2 and C3 indicated in Formula II is a single bond;
$R_5$ is H or =O; $R_6$ is H; and $R_7$ is OH, hydrogen, O-xylose, O-rhamnose or
Examples of the compounds are as follow: F199-C6, F199-C16, F199-C23, F199-C35, F199-C42, and F199-C57.

Formula III

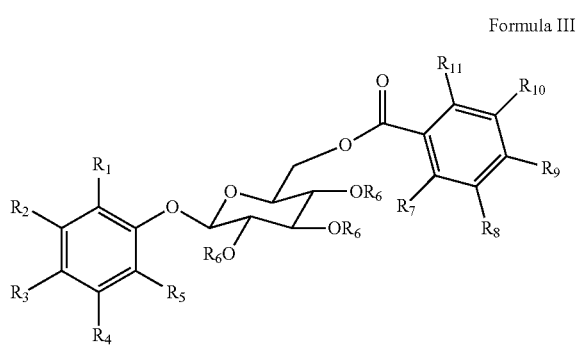

where $R_1$-$R_{11}$ are each independently unsubstituted (i.e., being hydrogen) or substituted with the same or independently different substituents deemed suitable by a person of ordinary skill in the art. Example of the compounds is as follow: F199-C34. There are other Cdk5 inhibitors of the present invention which are not of a structural formula II or III. Examples are as follows: F199-C4 and F199-C22. Detailed information about the structure of the compounds referenced here is provided later in this specification.

A further object of the present invention is to provide a method for treating or preventing diseases that are caused by aberrant changes in Cdk5's activities. Examples of such diseases are acute and chronic pain, diabetes mellitus, cancer, neurodegenerative disease and neuropathological disorders (such as AD, PD, ALS and Huntington's disease). The object is achieved by administering a therapeutically effective amount of compounds to patients as specified in the foregoing.

In addition to the effect on Cdk5, the treatment method of the present invention also protects neuronal cells from neurotoxicity and apoptosis induced by the amyloid beta peptide (Aβ). Aβ is a cleavage product derived from the amyloid precursor protein (APP), which accumulates as extracellular or senile plaques, the hallmark of AD. While the actual cause of AD remains elusive, Aβ has been implicated in many reports to play a part in the initiation and progression of the disease. Additionally, studies have shown that Aβ is neurotoxic, resulting in neuronal loss and subsequent memory loss and cognitive impairment.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

Preparation of Total Extract

Figure 1:
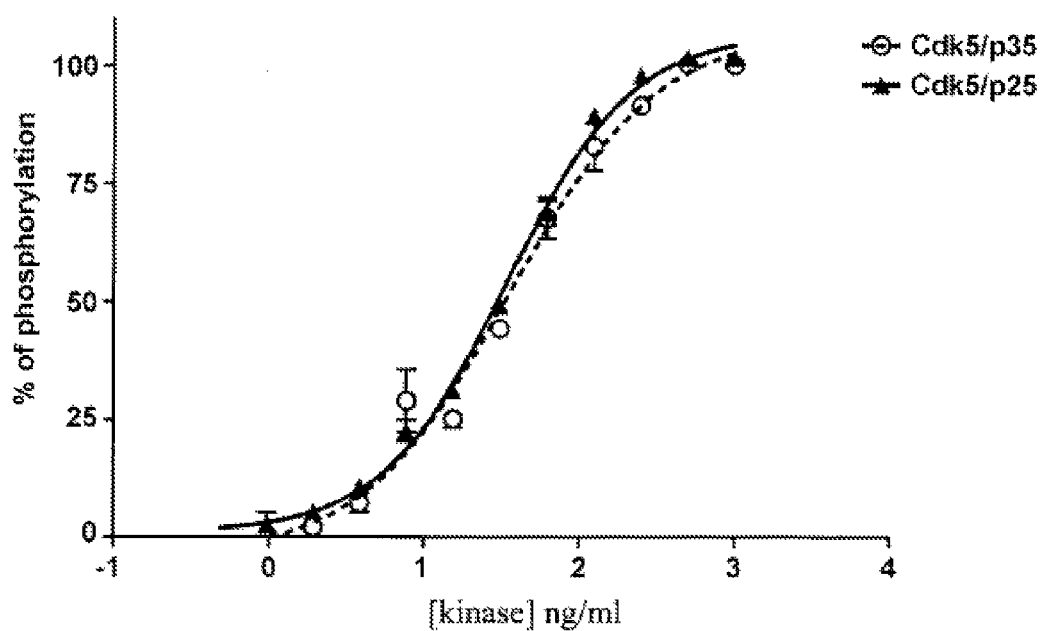
FIG. 1 presents the dose response curve of Cdk5/p25 and Cdk5/p35. Different concentrations of Cdk5/p25 or Cdk5/p35 were incubated with substrates and ATP for 1 hour. The assay was performed in quadruplicates.

The air-dried roots of *Rhodiola rosea* were harvested in October, 2005 at Yili, Xin-Jiang, China and purchased from Sichuan Medicinal Herb Ltd. (Chengdu, China) in October, 2005. The air-dried roots of *Rhodiola rosea* (300 g) was first dried and immersed in 1.5 L 70% ethanol (EtOH, material to solvent ratio at 1 to 5) for 30 mins. The herb-solvent mixture was then refluxed 3 times for 2 hours each. The extract was filtered and the filtrate was evaporated to dryness to give 44.0 g of the total extract (TE).

Preparation of Refined Fraction (F199-BU)

The TE (44.0 g) was dissolved/suspended in 300 mL water and sequentially extracted with chloroform (CF, 300 mL) and water-saturated butanol (BU, 300 mL) at 1 to 1 volume ratio. Extraction with each different solvent was repeated 5 times and the solvent extracts were filtered and dried to give fractions CF (14.5 g), BU (17.6 g), and water (WA, 10.2 g). HPLC parameters for F199-BU detection: HPLC conditions: High-performance liquid chromatography-diode array detection (HPLC-DAD) method has been developed for the analysis of and the quality control of F199-BU batch 090725T and F199-BU batch 080602T. Waters HPLC system consisting of a 600 pump, a 717 auto-sampler and a UV/VIS Photodiode Array 2996 Detector was used for all analyses. Chromatographic separations were carried out on a SunFire C18 column (Particle size 5 μm, 4.6 mm×150.0 mm) with acetonitrile (as Solvent A) and water (as Solvent B) in the mobile phase at a flow rate of 1.0 ml/min at room temperature. A gradient elution was applied from 10% to 60% of solvent A starting from 0 to 45 min (0-35 min, 10% to 50% ACN; 3540 min, 50% to 60% ACN; 4045 min, 60% to 10% ACN). Samples were filtered through a 0.45 μm Millipore syringe filter unit. Twenty microliter samples were injected for HPLC analysis.

Isolation of F199 Compounds

Compounds of this invention, with the identification code beginning with "F199", are isolated from *Rhodiola rosea* as described below, using a variety of reactions known to the skilled artisan. It is understood that one skilled in the art will also recognize that alternative methods may be employed to isolate the target compounds of this invention.

The air-dried roots of *Rhodiola rosea* were re-fluxed three times with 95% aqueous EtOH (35 L, 35 L, 35 L, 2 h/times). The 95% EtOH extract was concentrated in vacco to give a residue (900 g). The residue was suspended in $H_2O$ and then partitioned successively with petroleum ether, ethyl acetate and n-BuOH. Evaporation of these fractions resulted in a total of 90 g petroleum ether extract, 250 g EtOAc extract, and 360 g n-BuOH extract, respectively.

Then, the EtOAc extract (250 g) was first fractionated using a silica gel column eluted with the mixture of $CHCl_3$-MeOH with ascending polarity, and finally eluted with methanol to obtain 108 fractions (Fr.1-Fr.108). Depending on the TLC (Thin Layer Chromatography) pattern, similar fractions were combined. Compounds gallic acid (F199-C4, 18 mg) (from fraction Fr.21-22), rhodalin (F199-C6, 22 mg), litvinolin (F199-C16, 36 mg) (from Fr. 62-69), 6-O-galloyl rosin (F199-C22, 10 mg), 4'-methoxyherbacetin (F199-C23, 22 mg) (from Fr. 72-75), 6-O-galloyl arbutin (F199-C34, 17 mg), and epigallocatechin-3-gallate (F199-C35) (from Fr. 89-90) were isolated using repetitive column chromatography (silica gel or Sephadex LH-20) and recrystallization methods.

A part of n-BuOH extract (200 g) was subject to silica Gel column chromatography, eluting with EtOAc/EtOH/$H_2O$ with a ratio of 20:2:1, 16:2:1, 10:2:1, 6:2:1, 4:2:1, and then 66 fractions were obtained. Compounds kaempferol-3-O-β-D-xylopyranosyl(1→3)β-D-glucopyranoside (F199-C42, 9 mg) (from Fr. 12-14), and isomericitrin (F199-C57, 6 mg) (from Fr. 41-54) were isolated using repetitive column chromatography (silica gel or Sephadex LH-20, finally purity with preparative HPLC).

Cdk5 Kinase Assay and Kinetic Studies

Cdk5 kinase assay was performed as described in the instruction manual (Invitrogen, cat. no. PV3673). This assay employs a FRET-based, coupled-enzyme format and is based on the differential sensitivity of phosphorylated and non-phosphorylated peptides to proteolytic cleavage. The assay uses a synthetic peptide substrate (the Z'-LYTE™ peptide substrate) that is labeled with a donor fluorophore (coumarin) and an acceptor fluorophore (fluorescein) to make up a FRET pair. In the primary reaction, Cdk5 transfers the γ-phosphate of ATP to a serine/threonine residue on the substrate, while the presence of a kinase inhibitor in the primary reaction suppresses phosphorylation. In the secondary reaction, a site-specific protease (the Development Reagent) is added and cleaves non-phosphorylated Z'-LYTE™ peptide substrate at a substantially higher rate than phosphorylated substrate. Cleavage disrupts FRET between the donor and acceptor fluorophores on the non-phosphorylated substrate, while uncleaved phosphorylated substrate maintains FRET. The effectiveness of the compounds on inhibiting the Cdk5 activity is then measured by calculating the emission ratio.

Cdk5 kinase assay was performed by adding Z'-LYTE™ peptide substrate and ATP together with Cdk5/p25 or Cdk5/p35 kinase solution in a 384-well black polystyrene plate (Corning 3676). The plate was then incubated for one hour at room temperature. Development solution was then added in the dark for another hour. Finally, stop solution was added and the coumarin and fluorescein emission signals were measured on a fluorescence plate reader (Tecan, infinite F500) (excitation: 400 nM, emission 445 and 520 nM, respectively). To calculate the activity of cdk5/p25 and Cdk5/p35, Z'-LYTE phosphopeptide was used as a 100% phosphorylation control while nonphosphorylated Z'-LYTE peptide is used as a 0% phosphorylation control to establish the maximal and minimal emission ratio values which enable to calculate the percentage of kinase phosphorylation. To determine the inhibitory effect on cdk5 activity, fractions and compounds to be tested were included in the kinase reaction. Zero inhibition was determined by using DMSO (solvent) instead of the compounds in the reaction. Roscovitine, a well-known cdk5 inhibitor, was used as the positive control for the inhibition of kinase activity. Assays were done in quadruplicates and data was averaged from at least 4 independent experiments. Similar experimental protocols were performed for Cdk1/cyclin B and Cdk2/cyclin A kinase activity study. Activity of each kinase complex was evaluated by titration, and the resultant value of $EC_{30}$ was used in the inhibitory study. Since activity of kinase complexes varies with different batches of preparation, $EC_{30}$ will be determined in each new batch of kinases. $IC_{50}$ of the compounds on kinase complexes was determined in dose-dependent studies from an average of 3-5 individual experiments. Kinetic studies of compounds were performed by Cdk5/p25 kinase assays with various concentrations of ATP and tested compounds. The kinetic parameters were determined by a nonlinear least-squares program using GraphPad Prism 5 software.

Aβ Assay

Cortical neurons at 7 DIV in culture isolated from embryonic day 18 rats were used as cell models in the assay. Toxicity caused by Aβ25-35 peptide in these cells was evaluated by MTT detection after 2 days incubation. The Aβ assay was performed to investigate the ability of the invention to protect cortical neurons from cell death induced by exogenous Aβ25-35 peptide addition. Assays were done in duplicates and data was averaged from at least 3 independent experiments.

Animal Model of Pain

Adult ICR mice (6-8 week-old) habituated in the experimental room for 3 days before the testing. Testing was conducted from 9 am to 3 pm. Mice were randomly grouped and weighed. Mice were pretreated with a single dose of F199-C16 (10-100 mg/kg, intraperitoneal injection) and then injected with 10 μl of 2.5% formalin in the subplantar of the right hind paw. The licking time (in seconds) was recorded during 0-10 minutes (early phase) and in 11-40 minutes (late phase) after formalin injection. The whole process was monitored and recorded by a digital monochrome video camera. Data were expressed as the mean±SEM. (*p<0.05; ANOVA, with Student-Newman Keuls test).

Kinase Activity of Cdk5/p25 and Cdk5/p35

Kinase activity of Cdk5/p25 and Cdk5/p35 was measured using the Z'-LYTE™ Kinase Assay Kits (Invitrogen) as described above. The measurement data are shown in FIG. 1, which is in a form of dosage response curves. Different concentrations of Cdk5/p25 or Cdk5/p35 were incubated with substrates and ATP for 1 hour. As shown in FIG. 1, the kinase activity, indicated as the percentage of phosphorylation, increases with the increased concentration of the enzyme Cdk5/p25 and Cdk5/p35. As shown by the curve, $EC_{50}$ for Cdk5/p25 is about 35.8 ng/ml Cdk5/p25 is about 34.4 ng/ml.

Inhibitory Effects of Roscovitine on Cdk5 Measured in a FRET-Based Assay

Figure 2:
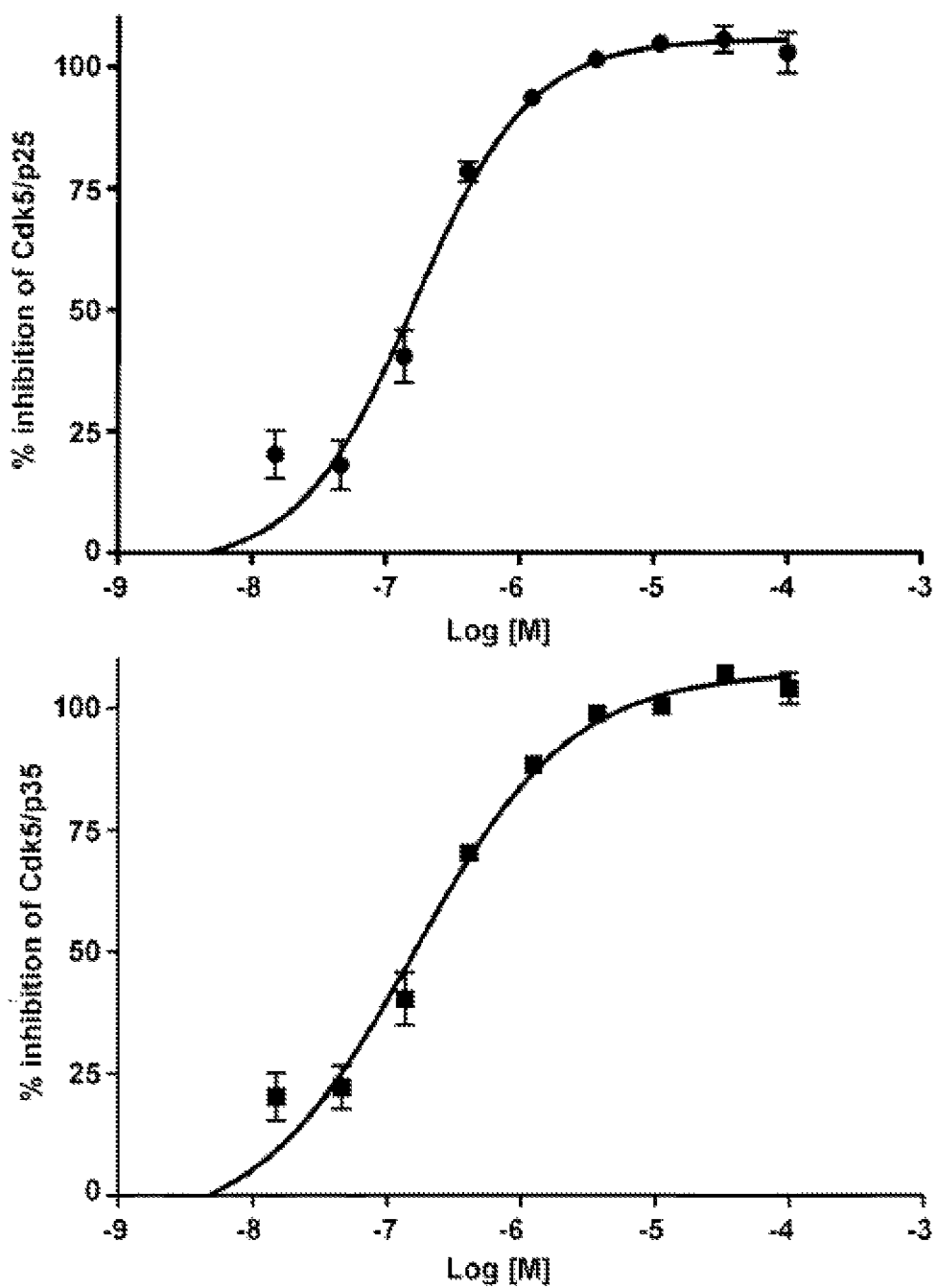
FIG. 2 shows inhibitory effect of roscovitine on Cdk5 kinase activity in a dose-dependent manner. Roscovitine at various concentrations were incubated with 30 ng/ml of Cdk5/p25 or Cdk5/p35. The assay was performed in quadruplicates.

Roscovitine (Ros) is a well-known Cdk5 kinase inhibitor. Its inhibitory effect on Cdk5/p35 and Cdk5/p25 was examined using Z'-LYTE™ Kinase Assay Kits (Invitrogen) as the positive control. FIG. 2 shows that roscovitine causes a decrease in Cdk5/p25 and Cdk5/p35 kinase activity in a dose-dependent manner, with $IC_{50}$=0.16 μM comparable to that reported in literature (Meijer et al., 1997).

Inhibitory Effects on Cdk5 of Compounds of the Present Invention

Using the FRET-based Cdk5 kinase assay method described above, the compounds of the present invention were examined for their inhibitory effects on Cdk5 kinase activity. The amount of Cdk5/25 and Cdk5/p35 used for screening Cdk5 inhibitors is $EC_{30}$ of the kinase complex and the $EC_{30}$ was determined with a titration study of kinase complex. The effectiveness of the compounds on inhibiting Cdk5 activity was then measured by comparing the percent phosphorylation of peptide substrates by Cdk5 kinase in the presence of test compounds and percent phosphorylation of peptide substrates by Cdk5 without test compounds.

Figure 3:
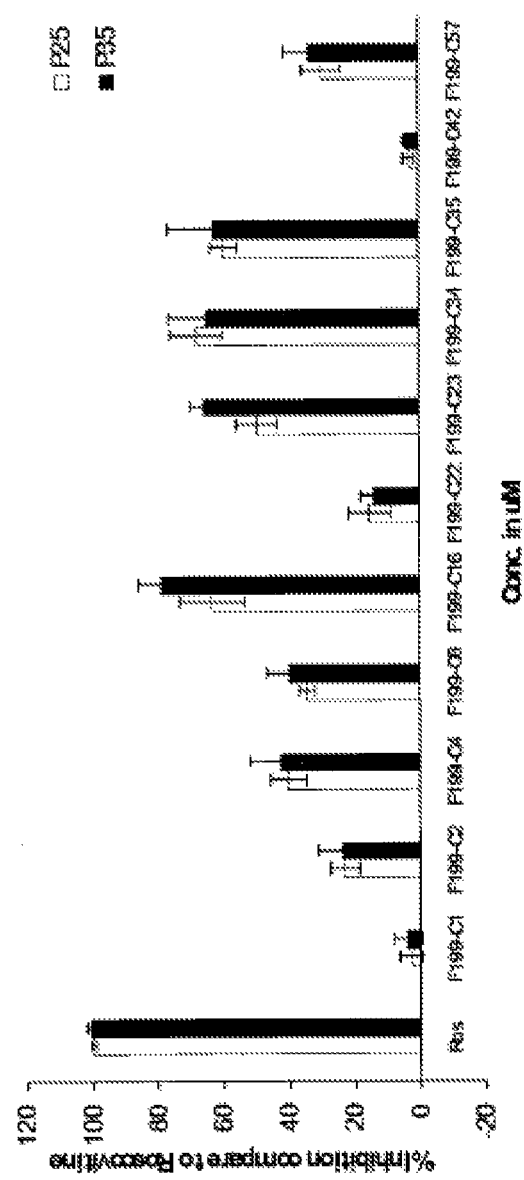
FIG. 3 shows inhibitory effect of the compounds of the present invention. Compounds (30 μM) were incubated with 30 ng/ml of Cdk5/p25 or Cdk5/p35. Roscovitine at 30 μM has 100% inhibition to both Cdk5/p25 and Cdk5/p35. Assays were performed in quadruplicates and data was averaged from 4 independent experiments

As shown in FIG. 3, eleven compounds isolated from *Rhodiola rosea* (F199) showed inhibitory effects on the kinase activity of Cdk5/p25 and Cdk5/p35, albeit to different extents. F199-C1 (daucosterol), F199-C22 (6-O-galloyl rosin, novel structure) and F199-C42 (kaempferol-3-O-β-D-xylopyranosyl(1→3)(3-D-glucopyranoside) showed weak inhibition (<25%) on Cdk5 activity. F199-C4 (gallic acid), F199-C6 (rodalin), and F199-C57 (isomericitrin) showed a moderate inhibition (25-50%), while F199-C16 (litvinolin), F199-C23 (4'-methoxyherbacetin), F199-C34 (6-O-galloyl arbutin), and F199-C35 (epigallocatechin-3-gallate) exhibited a strong inhibition (50-75%). F199-C1 (daucosterol) and F199-C2 (kaempferol) served as controls since they have been reported to moderately inhibit Cdk5 activity.

$IC_{50}$ and Maximal Inhibition

Figure 4:
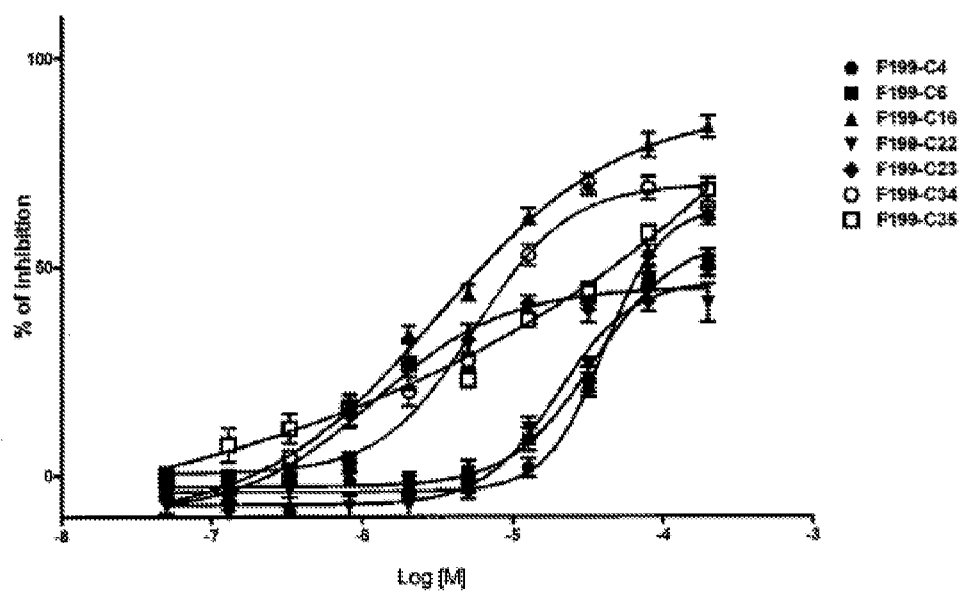
FIG. 4 shows dose dependent inhibitory effects on Cdk5/p25 activity by compounds of the present invention. Assays were done in quadruplicates and data was averaged from 4 independent experiments.

Seven natural compounds isolated from *Rhodiola rosea* (F199) were selected for $IC_{50}$ and maximal inhibition determination. Various concentrations of the F199 compounds were incubated with Cdk5/p25. The effectiveness of the compounds on inhibiting Cdk5 activity was then calculated by comparing the percent phosphorylation of peptide substrates by Cdk5/p25 in the presence of test compounds and percent phosphorylation of peptide substrates by Cdk5/p25 without test compounds. The results are presented in Table 1 and FIG. 4, which show that, of the seven compounds tested, F199-C16 (litvinolin) and F199-C34 (6-O-galloyl arbutin) have the lowest $IC_{50}$ and highest maximum inhibition to Cdk5/p25.

TABLE 1

| Compound | $IC_{50}$ (μM) | Maximum inhibition |
| --- | --- | --- |
| F199-C4 (gallic acid) | 40.6 | 64.19% at 200 μM |
| F199-C6 (rodalin) | 34.4 | 56.61% at 200 μM |
| F199-C16 (litvinolin) | 3.24 | 87.5% at 200 μM |
| F199-C22 (6-O-galloyl rosin, novel structure) | 20.1 | 46.5% at 80 μM |
| F199-C23 (4'-methoxy-herbacetin) | 1.21 | 45% at 20 μM |
| F199-C34 (6-O-galloyl arbutin) | 5.63 | 70% at 80 μM |
| F199-C35 (epigallocatechin-3-gallate) | 14.72 | 68.4% at 200 μM |

Effect of Anti-Excitotoxicity Induced by Aβ

Figure 5:
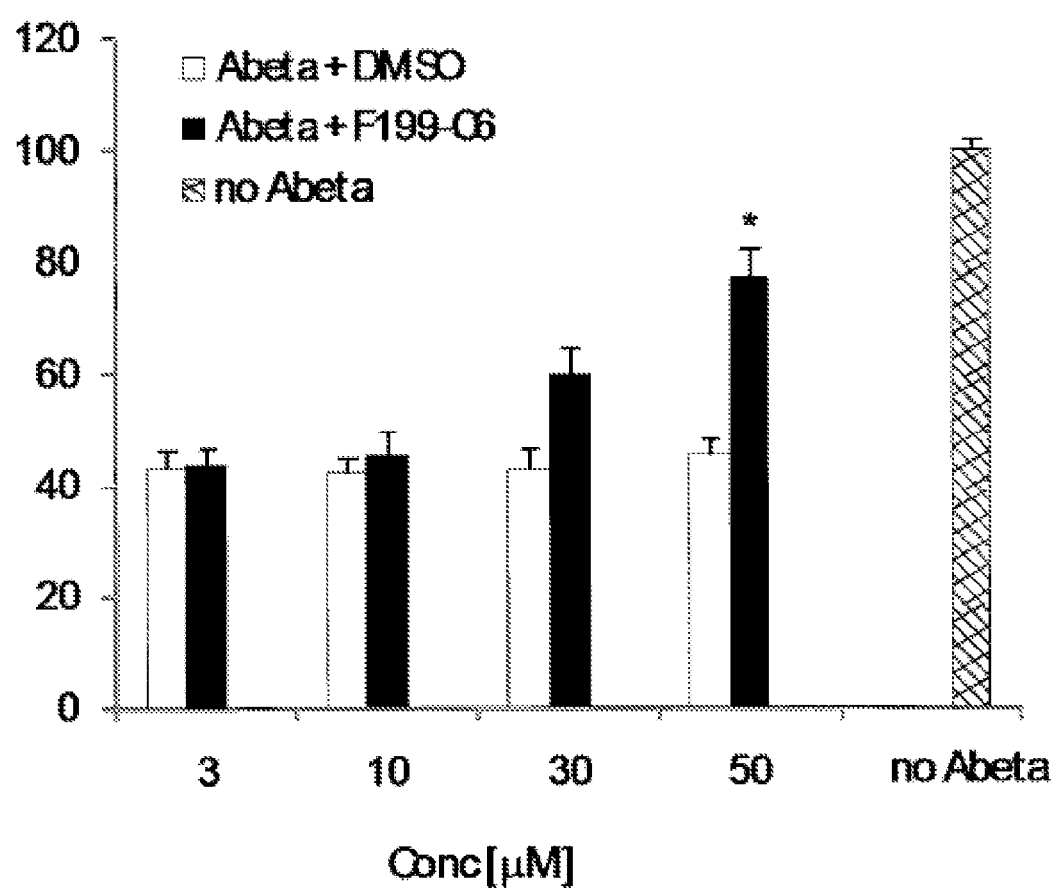
FIG. 5 shows a protective effect on rat cortical neurons against Aβ excitotoxicity by compound F199-C6. Embryonic rat cortical neurons (7 DIV) were pre-treated with various concentrations of compounds (3-50 μM) and then co-incubated with $Aβ_{25-35}$ (10 μM). After overnight incubation, the MTT assay was performed. Cell survival was calculated as a percentage compared to the vehicle control (DMSO). Assays were conducted in duplicates and data were compared with student-t test. *=P<0.05.
Figure 6:
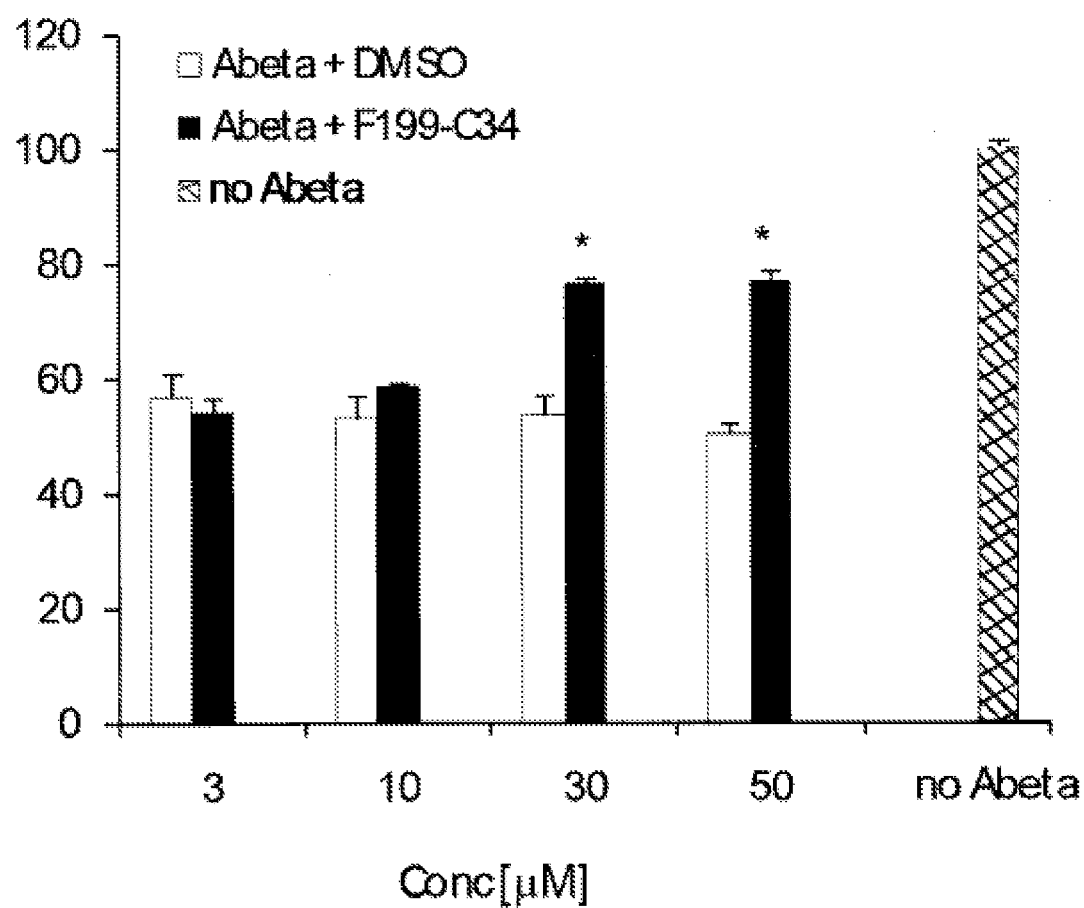
FIG. 6 shows a protective effect on rat cortical neurons against Aβ excitotoxicity by compound F199-C34 under the conditions as described for FIG. 5.
Figure 7:
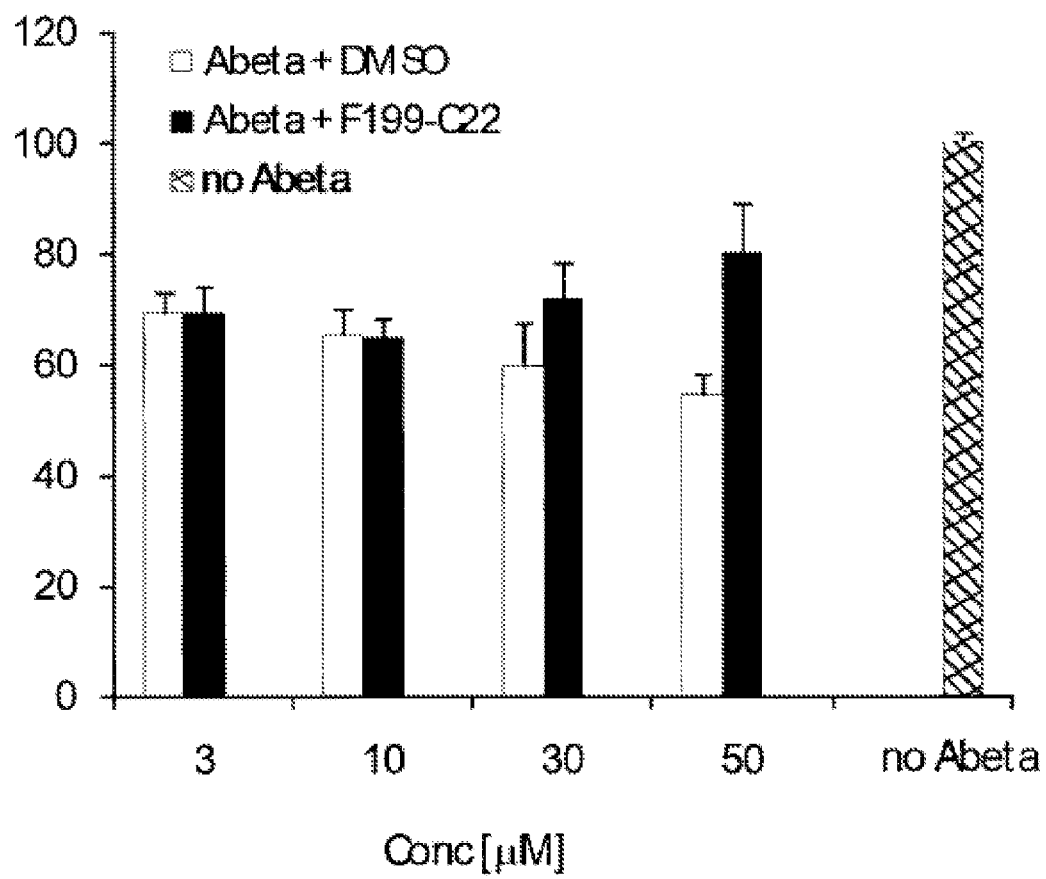
FIG. 7 shows a protective effect on rat cortical neurons against Aβ excitotoxicity by compound F199-C22 under the conditions as described for FIG. 5.

Exogenous addition of Aβ initiates cell death of neuronal cultures via apoptosis. The MTT assay, a well-known cell death assay, was performed to study the ability of the compounds of the present invention to prevent Aβ-induced excitotoxicity in primary cortical neuronal cells. Embryonic rat cortical neurons (7 DIV) were pre-treated with various concentrations of the compounds (3-50 μM) and then co-incubated with Aβ25-35 (10 μM). After overnight incubation, the MTT assay was performed. Cell survival was calculated as a percentage compared to the vehicle control (DMSO). Assays were conducted in duplicates and data were analyzed with student-t test. *=P<0.05. The results of exemplary compounds, F199-C6, F199-C34 and F199-C22 are presented in FIG. 5, FIG. 6 and FIG. 7, respectively. It is shown that those compounds at about 30 and 50 μM significantly promoted neuronal cell survival against Aβ toxicity compared to the DMSO control. These results demonstrate that the compounds of the present invention have significant effects in reducing the excitotoxicity induced by the Aβ.

Selectivity Among Different Cdks

Figure 8:
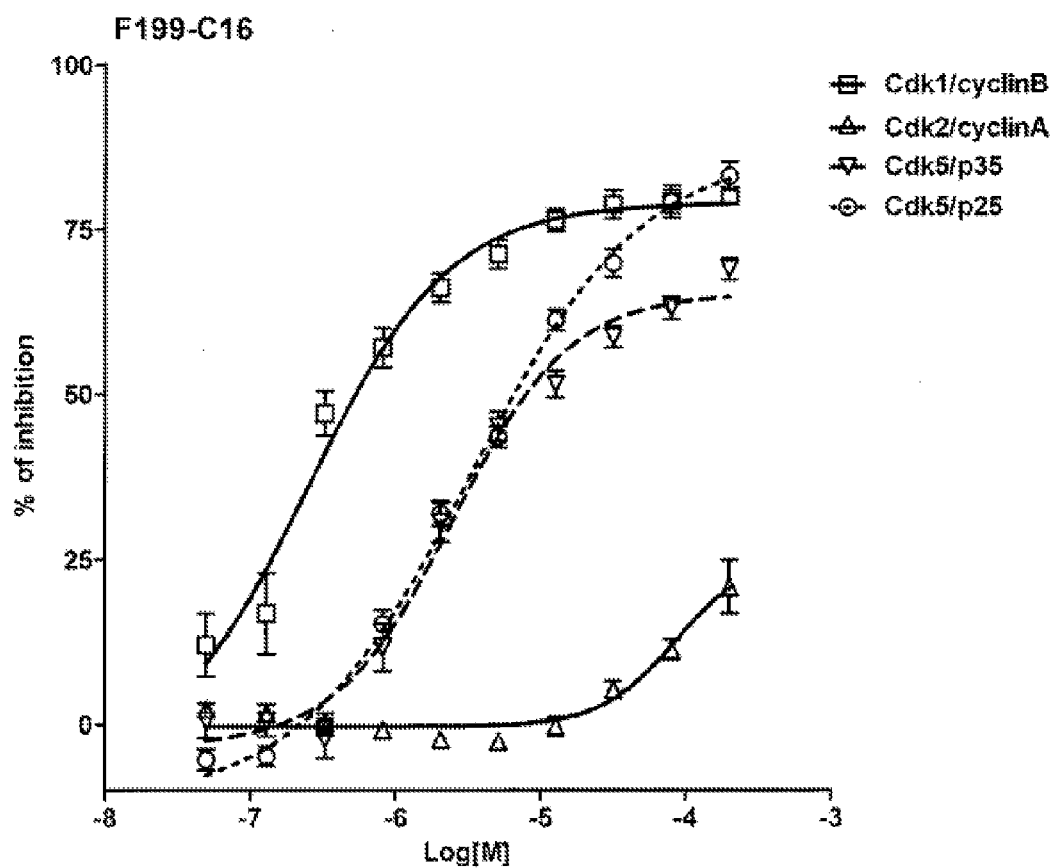
FIG. 8 shows differential inhibitory effects of F199-C16 on different Cdk complexes.
Figure 9:
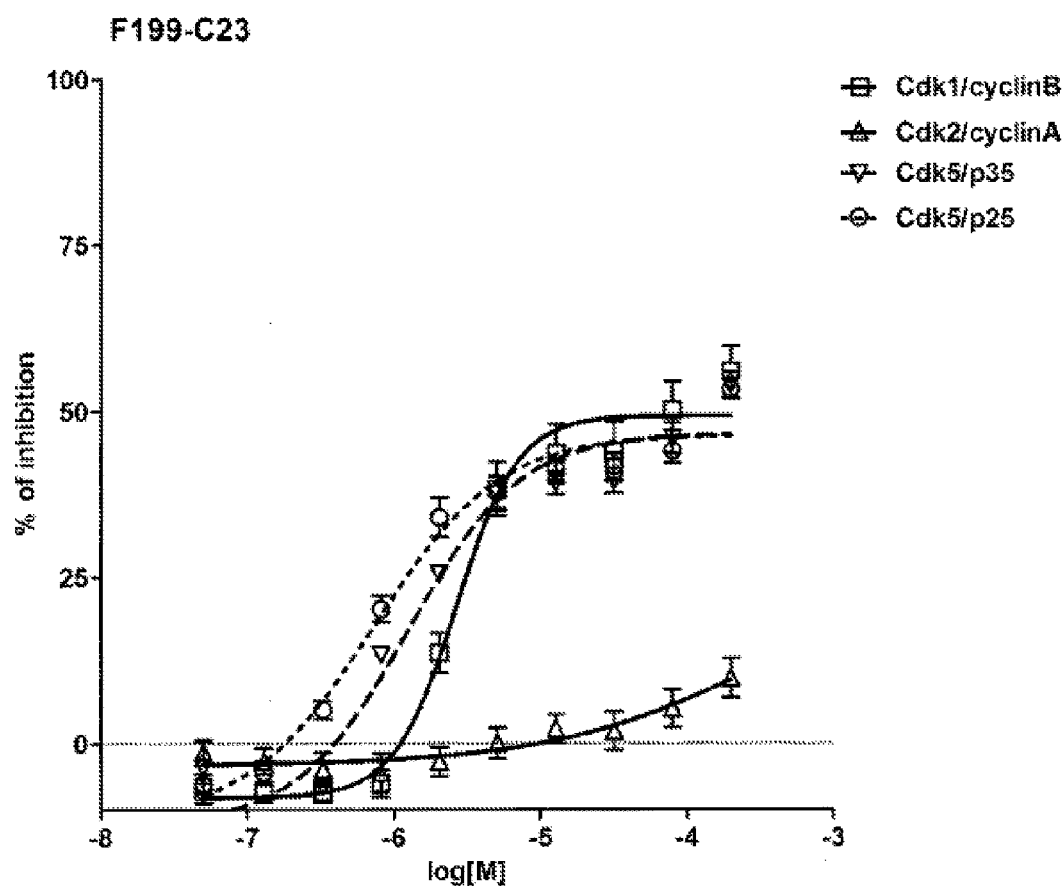
FIG. 9 shows differential inhibitory effect of F199-C23 on different Cdk complexes.
Figure 10:
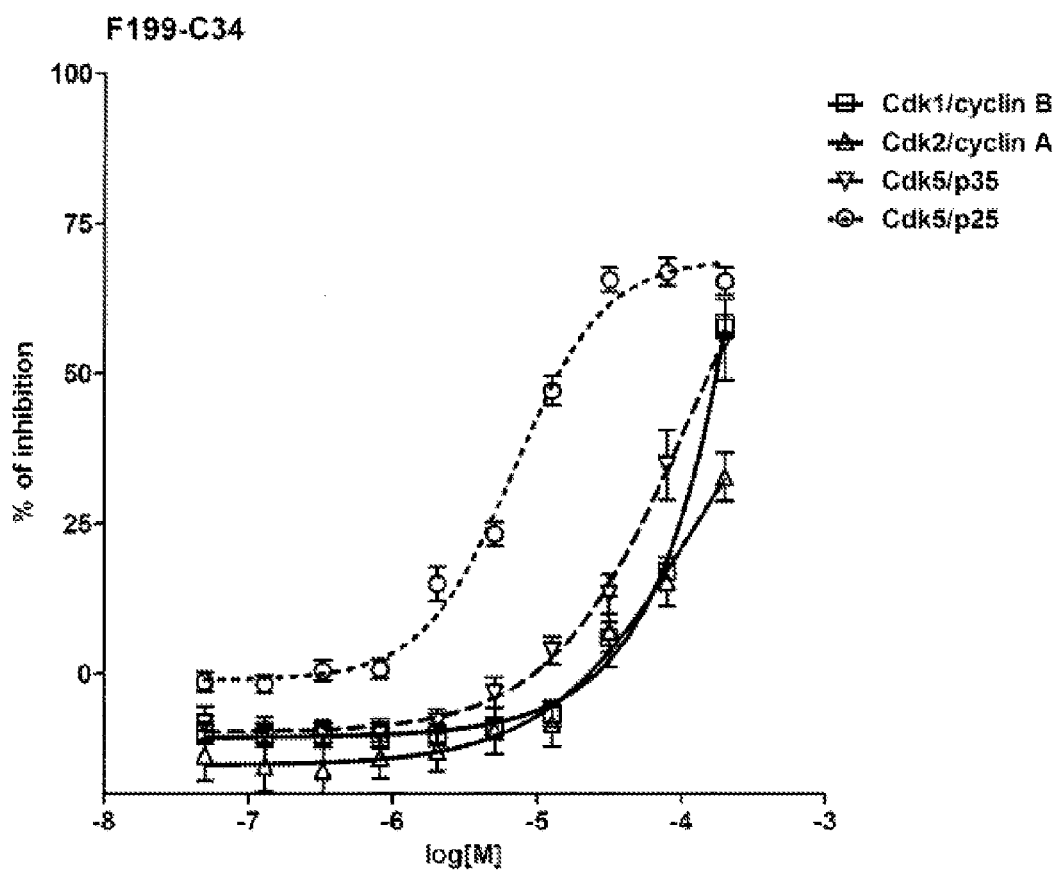
FIG. 10 shows differential inhibitory effect of F199-C34 on different Cdk complexes.

F199 compounds showed different selection or specificity among different types of Cdks, which can be useful information in developing therapeutic agents for different indications associated with different Cdks. FIG. 8 shows that while F199-C16 inhibited Cdk1/cyclin B complex potently, it exhibited milder inhibition on both Cdk5/p35 and Cdk5/p25. Inhibitory effect of F199-C16 on Cdk2/cyclin A was minimal. As shown in FIG. 9, F199-C23 inhibited similarly on Cdk1/cyclin B, Cdk5/p35 and Cdk5/p25 complexes, but its inhibitory effect on Cdk2/cyclin A was minimal. For F199-C34, while showing potent inhibitory effect on the Cdk5/p25 complex, it showed less effect on Cdk1/cyclin B, Cdk2/cyclin A, and Cdk5/p35 complexes.

Mixed-Type of Inhibition on Cdk5/p25 Complex

Figure 11:
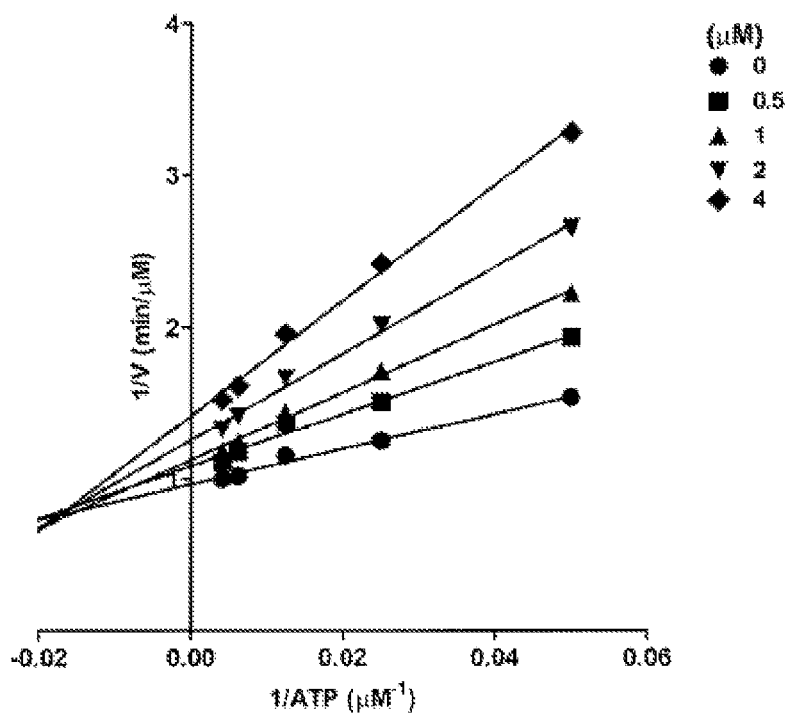
FIG. 11 shows the mode of inhibition of F199-C16 and F199-C23 on Cdk5/p25 complex.
Figure 11:
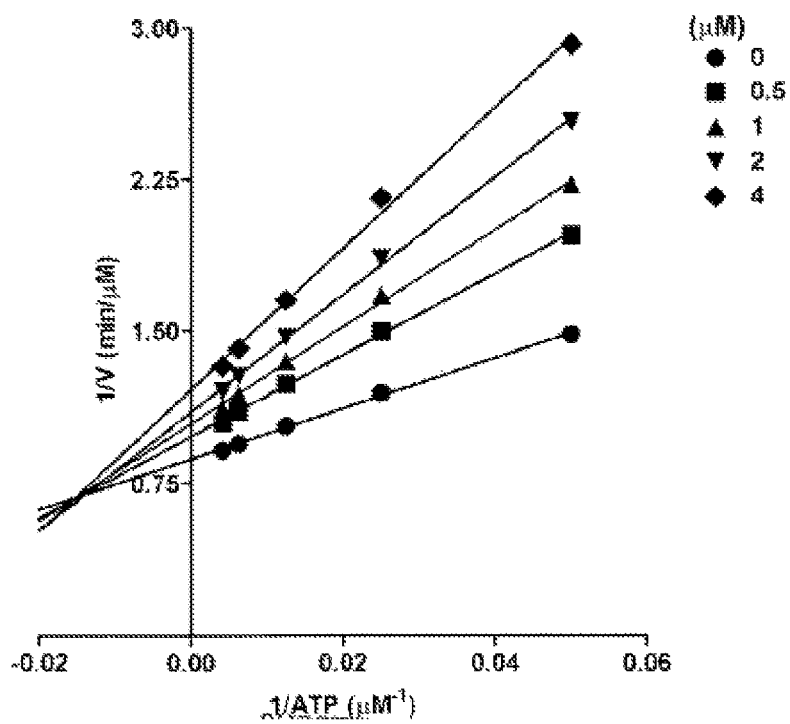
Figure 11:
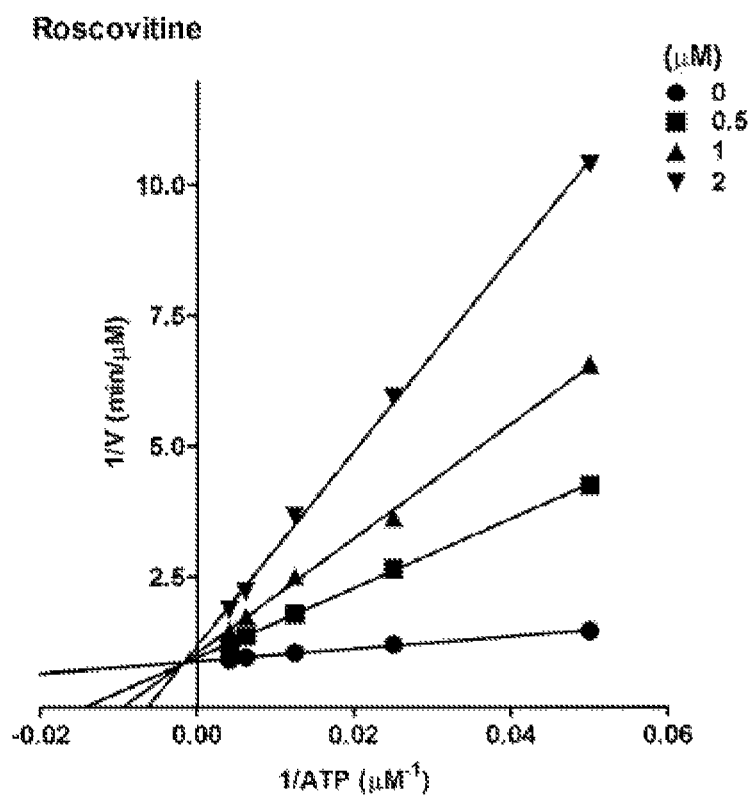

The inhibition mode of compounds, F199-C16 and F199-C23, at 0.5, 1, 2 and 4 µM was examined by measuring their effects on the pathological Cdk5/p25 complex in the presence of increasing concentrations of ATP using the FRET assay. FIG. 11 shows that both F199-C16 and F199-C23 exhibited a typical type of mixed inhibition on Cdk5/p25 complex, while roscovitine displayed a typical type of competitive inhibition.

Reduction of Paw-Licking Response in Pain Model

Figure 12:
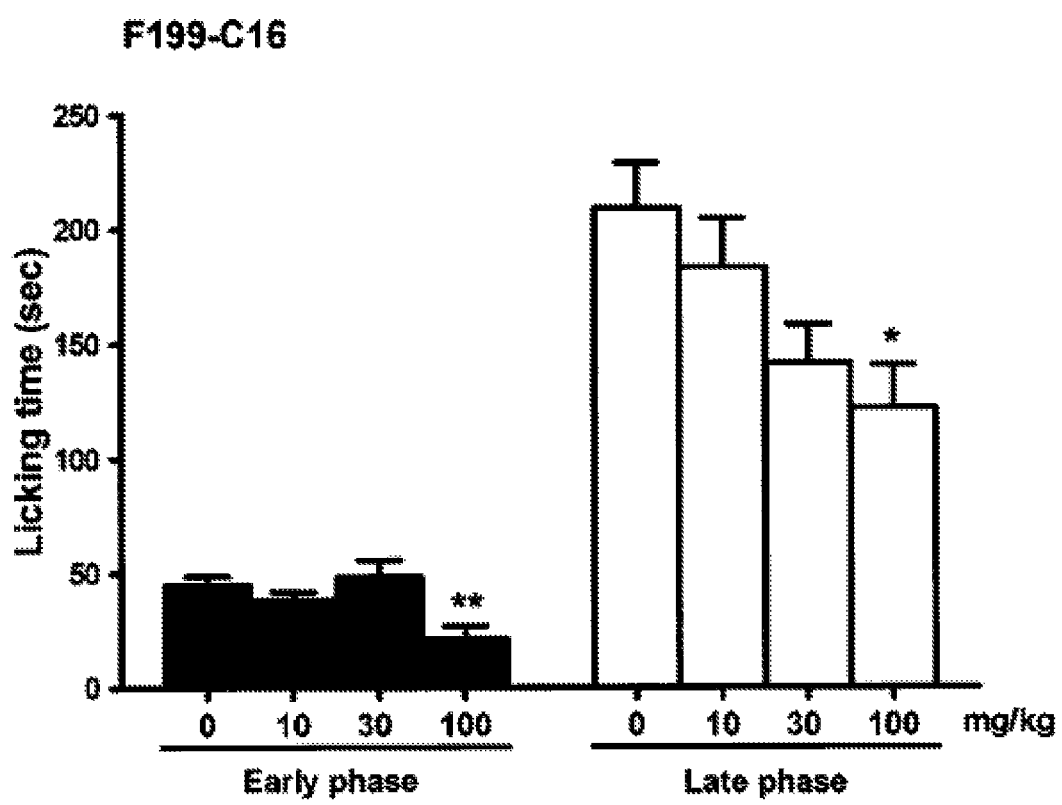
FIG. 12 shows the effect of F199-C16 on the paw-licking response in an animal model of pain.

The effect of F199-C16 was examined in an animal model of pain. The pain was induced by injecting formalin into the paw of the mouse. As shown in FIG. 12, F199-C16 reduced the licking time of right hind paw in a dose-dependent manner. At 100 mg/kg, the compound significantly reduced the licking time in both early (0-10 min) and late (11-40 min) phases of formalin-induced pain.

Effects of Total Extract and Various Fractions on Cdk5

Figure 13:
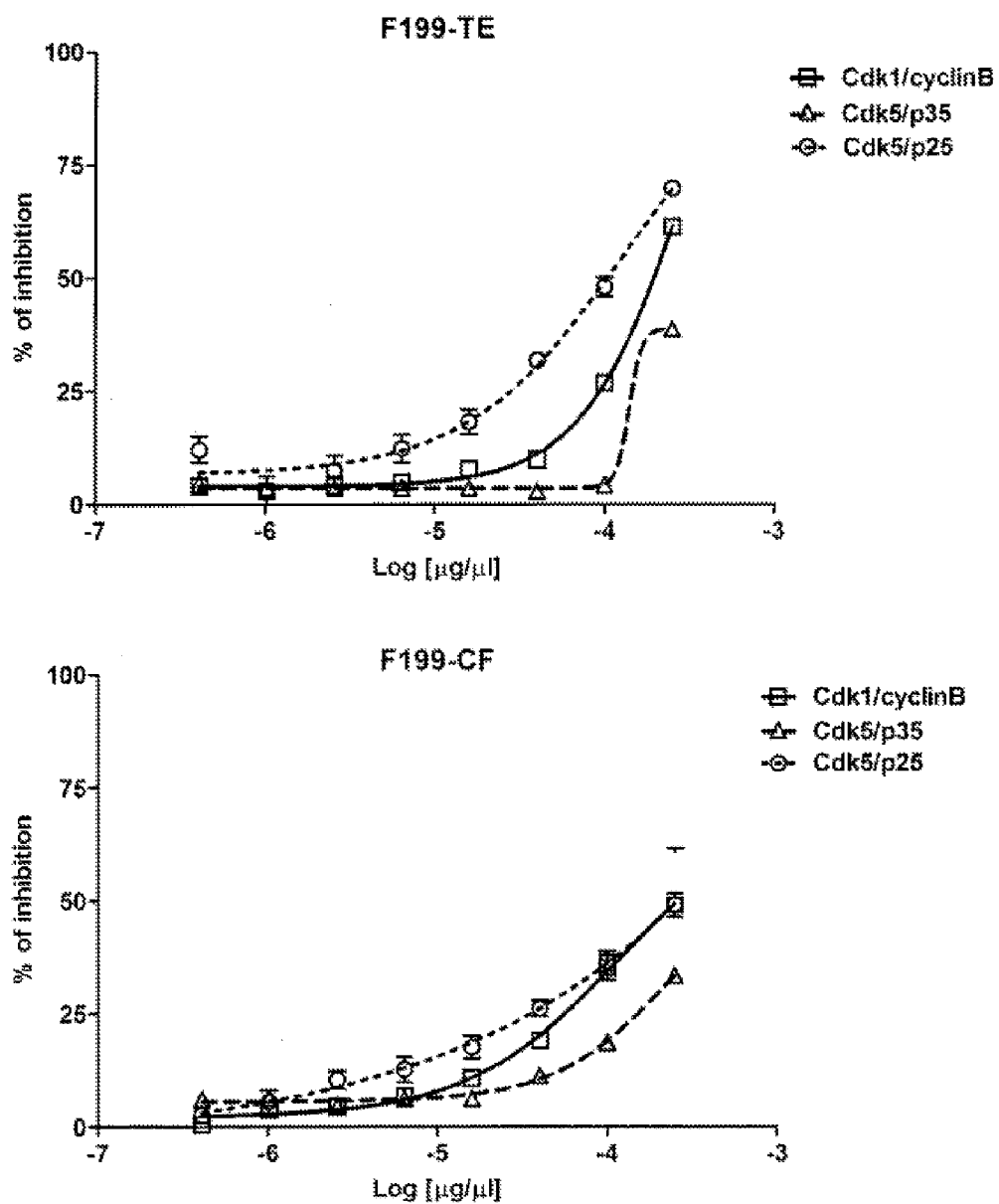
FIG. 13 shows the effects on Cdk5/p25 of total extract and various fractions of *Rhodiola rosea* of the present invention.
Figure 13:
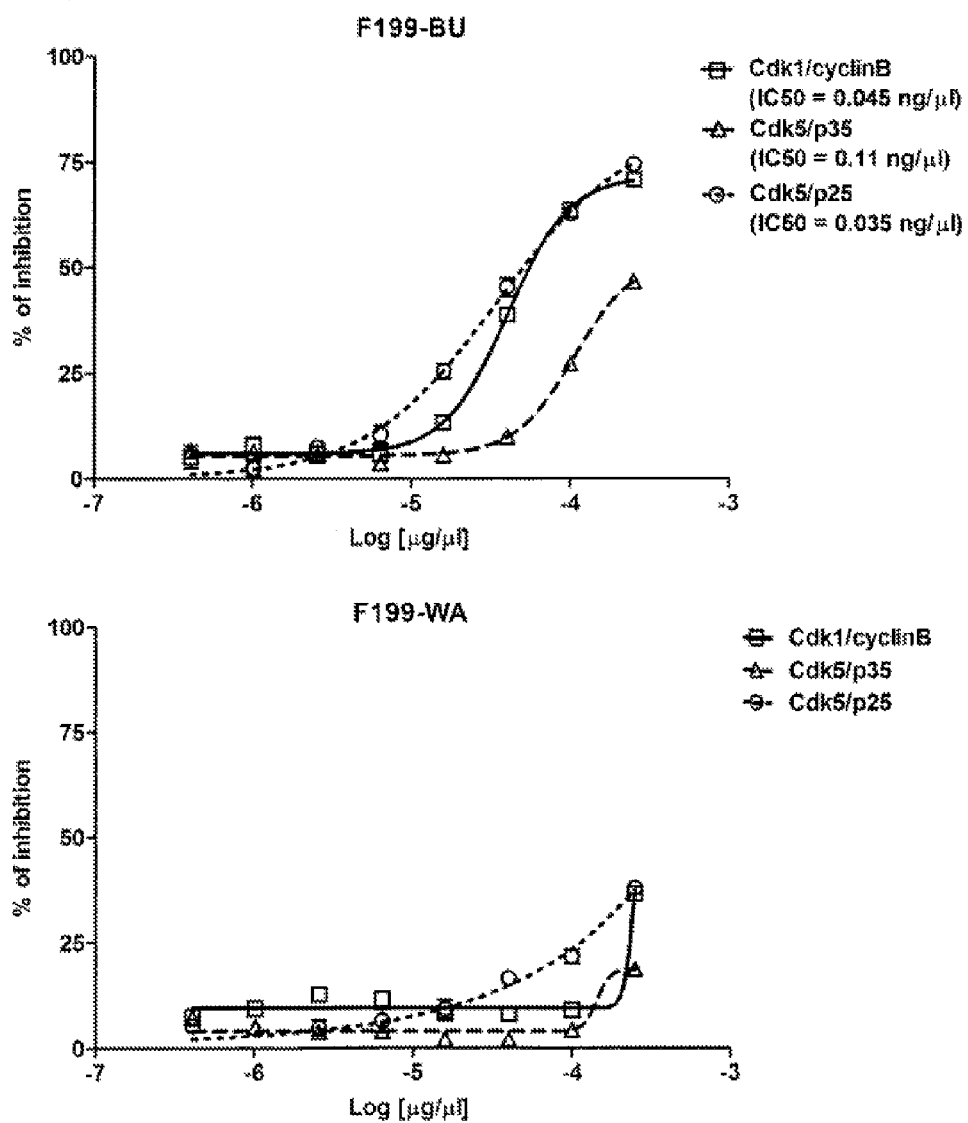

Total extract (TE) of *Rhodiola rosea* was prepared as described above. TE was then further fractionated using solvent partition, and 3 fractions, chloroform (CF), butanol (BU) and water (WA) were obtained. As shown in FIG. 13, F199-TE, F199-CF and F199-BU inhibited the pathological Cdk5/p25 and Cdk1/cyclin B more effectively than Cdk5/p35. While the $IC_{50}$ of F199-BU on Cdk1/cyclin B and Cdk5/p25 were 0.045 and 0.035 ng/µl, respectively, the $IC_{50}$ on Cdk5/p35 was 0.11 ng/µl.

HPLC Chromatograms of F199-BU

The refined fraction (F199-BU) prepared from *Rhodiola rosea* extract (F199-TE) exhibited Cdk5 inhibitory effect as described in FIG. 13. The protocol to prepare the refined fraction was described as the above. As shown in FIG. 14, the HPLC chromatograms of two batches of F199-BU (090725T and 080620T) were largely overlapped, indicating the fraction is highly reproducible and stable using our proprietry fractionation procedures.

Characterization of Compounds Isolated from *Rhodiola rosea*

Gallic Acid (F199-C4):

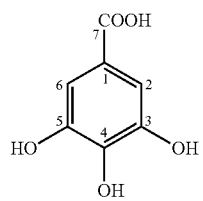

This compound has a molecular weight of 170 and molecular formula of $C_7H_6O_5$ on the basis of $^1H$ and $^{13}C$ NMR data in the following table, and is determined to be gallic acid.

| The $^1H$ and $^{13}C$ NMR data of compound gallic acid | | |
|---|---|---|
| Position | $^1H$ NMR | $^{13}C$ NMR |
| 1 | | 121.78 |
| 2 | 7.05 (1H, s) | 110.16 |
| 3 | | 146.16 |
| 4 | | 139.38 |
| 5 | | 146.16 |
| 6 | 7.05 (1H, s) | 110.16 |
| 7 | | 170.15 |

Rhodalin (F199-C6):

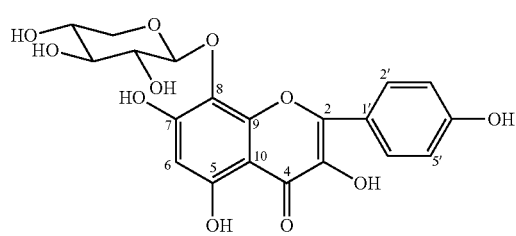 [SMILES: O=c1c(O)c(-c2ccc(O)cc2)oc2c(OC3OCC(O)C(O)C3O)c(O)cc(O)c12]

This compound has a molecular weight of 434 and molecular formula of $C_{20}H_{18}O_{11}$ on the basis of $^1H$ and $^{13}C$ NMR data in the following table, and is determined to be rhodalin.

| The $^1H$ and $^{13}C$ NMR data of compound rhodalin (CD$_3$OD) | | |
|---|---|---|
| Position | $^1H$ NMR | $^{13}C$ NMR |
| 2 | | 148.02 |
| 3 | | 137.03 |
| 4 | | 177.12 |
| 5 | | 149.89 |
| 6 | 6.23 (1H, s) | 99.31 |
| 7 | | 149.90 |
| 8 | | 126.07 |
| 9 | | 148.02 |
| 10 | | 104.29 |
| 1' | | 123.67 |
| 2' | 8.34 (1H, d, J = 8.8 Hz) | 131.16 |
| 3' | 6.89 (1H, d, J = 8.8 Hz) | 116.12 |
| 4' | | 160.41 |
| 5' | 6.89 (1H, d, J = 8.8 Hz) | 116.12 |
| 6' | 8.34 (1H, d, J = 8.8 Hz) | 131.15 |
| Xyl | | |
| 1" | 4.69 (1H, d, J = 7.6 Hz) | 104.30 |
| 2" | 3.60 (1H, m) | 75.16 |
| 3" | 3.40 (1H, m) | 77.47 |
| 4" | 3.60 (1H, m) | 70.92 |
| 5" | 3.93 (1H, dd, J = 5.2, 11.2 Hz) | 67.40 |
| | 3.22 (1H, t, J = 11.2 Hz) | |

Litvinolin (F199-C16):

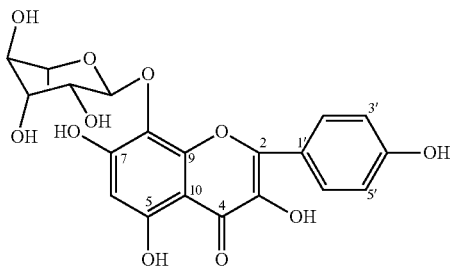 [SMILES: CC1OC(Oc2c(O)cc(O)c3c(=O)c(O)c(-c4ccc(O)cc4)oc23)C(O)C(O)C1O]

This compound has a molecular weight of 448 and molecular formula of $C_{21}H_{20}O_{11}$ on the basis of $^1H$ and $^{13}C$ NMR data in the following table, and is determined to be litvinolin.

| The $^1H$ and $^{13}C$ NMR data of compound litvinolin (DMSO) | | |
|---|---|---|
| Position | $^1H$ NMR | $^{13}C$ NMR |
| 2 |  | 147.44 |
| 3 | 8.78 (1H, brs OH) | 135.81 |
| 4 |  | 176.41 |
| 5 | 11.90 (1H, brs OH) | 151.66 |
| 6 | 6.59 (1H, s) | 98.38 |
| 7 | 9.45 (1H, brs OH) | 148.02 |
| 8 |  | 127.13 |
| 9 |  | 144.54 |
| 10 |  | 104.61 |
| 1' |  | 121.83 |
| 2' | 8.15 (1H, brs) | 129.83 |
| 3' | 6.95 (1H, brs) | 115.46 |
| 4' | 10.13 (1H, brs, OH) | 159.39 |
| 5' | 6.95 (1H, brs) | 115.46 |
| 6' | 8.15 (1H, brs) | 129.83 |
| Rha |  |  |
| 1'' | 5.48 (1H, brs) | 99.49 |
| 2'' | 3.95 (1H, m) | 70.11 |
| 3'' | 3.82 (1H, m) | 70.11 |
| 4'' | 3.34 (1H, m) | 71.78 |
| 5'' | 3.82 (1H, m) | 69.93 |
| 6'' | 1.23 (3H, brs) | 17.91 |

6-O-Galloyl Rosin (F199-C22):

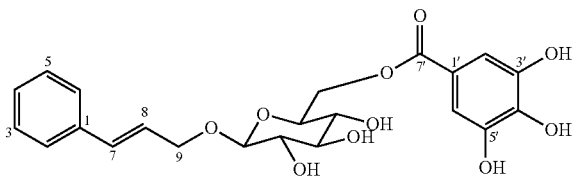 [SMILES: O=C(OCC1OC(OC/C=C/c2ccccc2)C(O)C(O)C1O)c1cc(O)c(O)c(O)c1]

This compound has a molecular weight of 448 and molecular formula of $C_{22}H_{24}O_{10}$ on the basis of $^1H$ and $^{13}C$ NMR data in the following table, and is determined to be 6-O-galloyl rosin.

| The $^1H$ and $^{13}C$ NMR data of compound 6-O-galloyl rosin (CD$_3$OD) | | |
|---|---|---|
| Position | $^1H$ NMR | $^{13}C$ NMR |
| 1 |  | 138.29 |
| 2 | 7.34 (1H, d, J = 7.6 Hz) | 127.74 |
| 3 | 7.24 (1H, t, J = 7.6 Hz) | 129.72 |
| 4 | 7.18 (1H, brd, J = 7.6 Hz) | 128.87 |
| 5 | 7.24 (1H, t, J = 7.6 Hz) | 129.72 |
| 6 | 7.34 (1H, d, J = 7.6 Hz) | 127.74 |
| 7 | 6.57 (1H, d, J = 16.0 Hz) | 134.43 |
| 8 | 6.33 (1H, ddd, J = 16.0, 5.6, 1.2 Hz) | 126.59 |
| 9 | 4.42 (1H, m) | 72.04 |
|  | 4.27 (1H, m) |  |
| Glc-1 | 4.40 (1H, d, J = 8.0 Hz) | 103.38 |
| Glc-2 | 3.26 (1H, m) | 75.76 |
| Glc-3 | 3.33 (1H, m) | 78.72 |
| Glc-4 | 3.43 (1H, m) | 70.97 |
| Glc-5 | 3.53 (1H, m) | 75.33 |
| Glc-6 | 4.55 (1H, dd, 12.0, 2.0) | 65.02 |
|  | 4.44 (1H, dd, 12.0, 5.6) |  |
| 1' |  | 121.70 |
| 2' | 7.11 (1H, s) | 110.43 |
| 3' |  | 146.78 |
| 4' |  | 140.00 |
| 5' |  | 146.78 |
| 6' | 7.11 (1H, s) | 110.43 |
| 7' |  | 168.50 |

4'-Methoxyherbacetin (F199-C23):

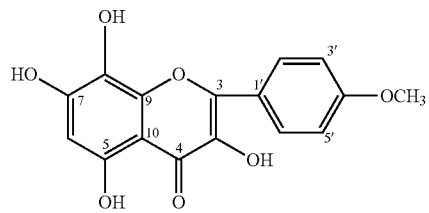 [SMILES: COc1ccc(-c2oc3c(O)c(O)cc(O)c3c(=O)c2O)cc1]

This compound has a molecular weight of 316 and molecular formula of $C_{16}H_{12}O_7$ on the basis of $^1H$ and $^{13}C$ NMR data in the following table, and is determined to be 4'-methoxyherbacetin.

| The 1H and 13C NMR data of compound 4'-methoxyherbacetin (DMSO) | | |
|---|---|---|
| Position | $^1H$ NMR | $^{13}C$ NMR |
| 2 |  | 154.53 |
| 3 |  | 136.00 |
| 4 |  | 178.18 |
| 5 |  | 155.00 |
| 6 | 6.49 (1H, s) | 95.82 |
| 7 |  | 148.80 |
| 8 |  | 127.89 |
| 9 |  | 145.47 |
| 10 |  | 105.10 |
| 1' |  | 124.23 |
| 2' | 8.22 (1H, d, J = 8.0 Hz) | 131.31 |
| 3' | 6.93 (1H, d, J = 8.0 Hz) | 116.57 |
| 4' |  | 160.94 |
| 5' | 6.93 (1H, d, J = 8.0 Hz) | 116.57 |
| 6' | 8.22 (1H, d, J = 8.0 Hz) | 131.31 |
| 4'-OCH$_3$ | 3.97 | 57.28 |

6-O-Galloyl Arbutin (F199-C34):

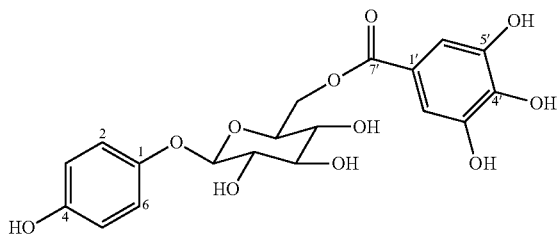 [SMILES: O=C(OCC1OC(Oc2ccc(O)cc2)C(O)C(O)C1O)c1cc(O)c(O)c(O)c1]

This compound has a molecular weight of 424 and molecular formula of $C_{19}H_{20}O_{11}$ on the basis of $^1H$ and $^{13}C$ NMR data in the following table, and is determined to be 6-O-galloyl arbutin.

| The $^1H$ and $^{13}C$ NMR data of compound 6-O-galloyl arbutin (CD$_3$OD) | | |
|---|---|---|
| Position | $^1H$ NMR | $^{13}C$ NMR |
| 1 | | 153.96 |
| 2 | 6.90 (1H, d, J = 8.8 Hz) | 116.88 |
| 3 | 6.60 (1H, d, J = 8.8 Hz) | 119.62 |
| 4 | | 152.56 |
| 5 | 6.60 (1H, d, J = 8.8 Hz) | 119.62 |
| 6 | 6.90 (1H, d, J = 8.8 Hz) | 116.88 |
| Glc-1 | 4.70 (1H, d, J = 6.8 Hz) | 103.98 |
| Glc-2 | 3.38 (1H, m) | 75.70 |
| Glc-3 | 3.44 (1H, m) | 78.07 |
| Glc-4 | 3.46 (1H, m) | 71.99 |
| Glc-5 | 3.68 (1H, m) | 75.14 |
| Glc-6 | 4.57 (1H, brd, J = 11.6 Hz) | 65.05 |
| | 4.41 (1H, dd, J = 11.6, 6.8 Hz) | |
| 1' | | 121.57 |
| 2' | 7.11 (1H, s) | 110.46 |
| 3' | | 146.71 |
| 4' | | 140.09 |
| 5' | | 146.71 |
| 6' | 7.11 (1H, s) | 110.46 |
| 7' | | 168.43 |

Epigallocatechin-3-Gallate (F199-C35):

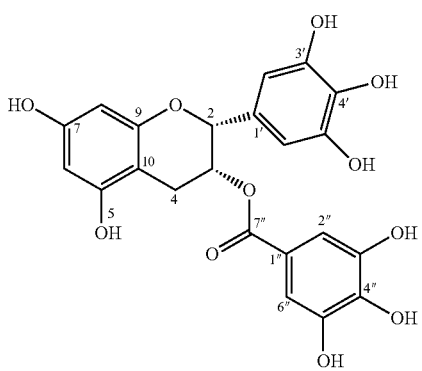 [SMILES: O=C(O[C@@H]1Cc2c(O)cc(O)cc2O[C@@H]1c1cc(O)c(O)c(O)c1)c1cc(O)c(O)c(O)c1]

This compound has a molecular weight of 458 and molecular formula of $C_{22}H_{18}O_{11}$ on the basis of $^1H$ and $^{13}C$ NMR data in the following table, and is determined to be epigallocatechin-3-gallate.

| The $^1H$ and $^{13}C$ NMR data of compound epigallocatechin-3-gallate (CD$_3$OD) | | |
|---|---|---|
| Position | $^1H$ NMR | $^{13}C$ NMR |
| 2 | 4.96 (1H, s) | 78.77 |
| 3 | 5.52 (1H, brs) | 70.11 |
| 4 | 2.97 (1H, dd, J = 17.2, 4.4 Hz) | 27.00 |
| | 2.83 (1H, dd, J = 17.2, 2.4 Hz) | |
| 5 | | 158.02 |
| 6 | 5.95 (1H, s) | 96.70 |
| 7 | | 157.98 |
| 8 | 5.95 (1H, s) | 96.05 |
| 9 | | 157.38 |
| 10 | | 99.61 |
| 1' | | 130.98 |
| 2' | 6.50 (1H, s) | 107.06 |
| 3' | | 146.84 |
| 4' | | 133.94 |
| 5' | | 146.84 |
| 6' | 6.50 (1H, s) | 107.06 |
| 1" | | 121.68 |
| 2" | 6.94 (1H, s) | 110.44 |
| 3" | | 146.44 |
| 4" | | 139.95 |
| 5" | | 146.44 |
| 6" | 6.94 (1H, s) | 110.44 |
| 7" | | 167.83 |

Kaempferol-3-O-β-D-Xylopyranosyl(1→3)β-D-Glucopyranoside
(F199-C42):

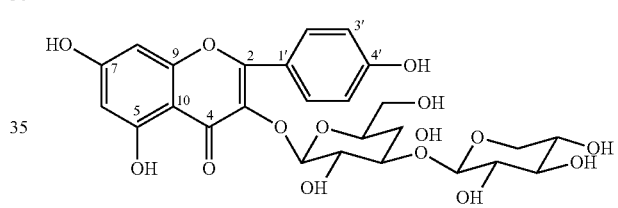

This compound has a molecular weight of 580 and molecular formula of $C_{26}H_{28}O_{15}$ on the basis of $^1H$ and $^{13}C$ NMR data in the following table, and is determined to be kaempferol-3-O-β-D-xylopyranosyl(1→3)β-D-glucopyranoside.

| The $^1H$ and $^{13}C$ NMR data of compound kaempferol-3-O-β-D-xylopyranosyl(1→3)β-D-glucopyranoside (CD3OD) | | |
|---|---|---|
| Position | $^1H$ NMR | $^{13}C$ NMR |
| 2 | | 158.52 |
| 3 | | 135.14 |
| 4 | | 179.73 |
| 5 | | 158.52 |
| 6 | 6.18 (1H, brs) | 99.94 |
| 7 | | 165.83 |
| 8 | 6.37 (1H, brs) | 94.82 |
| 9 | | 163.19 |
| 10 | | 105.96 |
| 1' | | 122.99 |
| 2' | 8.04 (1H, d, J = 8.4 Hz) | 132.47 |
| 3' | 6.88 (1H, d, J = 8.4 Hz) | 116.43 |
| 4' | | 161.55 |
| 5' | 6.88 (1H, d, J = 8.4 Hz) | 116.43 |
| 6' | 8.04 (1H, d, J = 8.4 Hz) | 132.47 |
| Glc-1 | 5.46 (1H, d, J = 7.6 Hz) | 100.92 |
| Glc-2 | 3.22 (1H, m) | 75.08 |
| Glc-3 | 3.34 (1H, m) | 82.47 |
| Glc-4 | 3.33 (1H, m) | 71.22 |
| Glc-5 | 3.50 (1H, m) | 77.24 |

-continued

The $^1$H and $^{13}$C NMR data of compound kaempferol-3-O-β-D-xylopyranosyl(1→3)β-D-glucopyranoside (CD3OD)

| Position | $^1$H NMR | $^{13}$C NMR |
|---|---|---|
| Glc-6 | 4.29, 3.96 (each, 1H, m) | 62.56 |
| Xyl-1 | 4.75 (1H, d, J = 6.8 Hz) | 105.53 |
| Xyl-2 | 3.50 (1H, m) | 75.18 |
| Xyl-3 | 3.52 (1H, m) | 78.41 |
| Xyl-4 | 3.53 (1H, m) | 71.16 |
| Xyl-5 | 3.85, 3.16 (each, 1H, m) | 66.83 |

Isomericitrin (F199-C57):

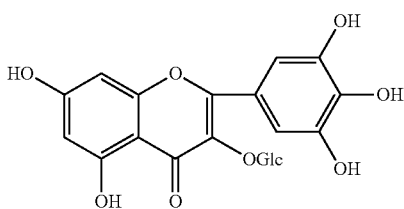

This compound has a molecular weight of 460 and molecular formula of $C_{21}H_{16}O_{12}$ on the basis of $^1$H and $^{13}$C NMR data in the following table, and is determined to be isomericitrin.

The $^1$H NMR data of compound isomericitrin (DMSO)

| Position | $^1$H NMR |
|---|---|
| 2 | |
| 3 | |
| 4 | |
| 5 | |
| 6 | 6.20 (1H, d, J = 2.0 Hz) |
| 7 | |
| 8 | 6.38 (1H, d, J = 2.0 Hz) |
| 9 | |
| 10 | |
| 1' | |
| 2' | 7.29 (1H, s) |
| 3' | |
| 4' | |
| 5' | |
| 6' | 7.29 (1H, s) |
| Glc-1 | 5.23 (1H, d, J = 7.6 Hz) |
| Glc-2 | 3.35 (1H, m) |
| Glc-3 | 3.47 (1H, m) |
| Glc-4 | 3.41 (1H, m) |
| Glc-5 | 3.51 (1H, m) |
| Glc-6 | 3.73 (1H, dd, J = 12.0, 2.4 Hz) |
| | 3.61 (1H, dd, J = 12.0, 4.8 Hz) |

REFERENCES

Anne, S. L., Saudou, F. and Humbert, S. (2007). Phosphorylation of huntingtin by cyclin-dependent kinase 5 is induced by DNA damage and regulates wild-type and mutant huntingtin toxicity in neurons. J Neurosci 27, 7318-7328.

Bajaj, N. P., Al-Sarraj, S. T., Anderson, V., Kibble, M, Leigh, N. and Miller, C. C. (1998). Cyclin-dependent kinase-5 is associated with lipofuscin in motor neurones in amyotrophic lateral sclerosis. Neurosci Lett 245, 45-48.

Chergui, K., Svenningsson, P. and Greengard, P. (2004). Cyclin-dependent kinase 5 regulates dopaminergic and glutamatergic transmission in the striatum. Proc Natl Acad Sci USA 101, 2191-2196.

Cheung, Z. H. and Ip, N. Y. (2004). Cdk5: mediator of neuronal death and survival. Neurosci Lett 361, 47-51.

Cheung, Z. H., Fu, A. K. Y. and Ip, N. Y. (2006). Synaptic Roles of Cdk5: Implications in Higher Cognitive Functions and Neurodegenerative Diseases. Neuron 50, 13.

Connell-Crowley L., Le Gall, M., Vo, D. J. and Giniger, E. (2000). The cyclin-dependent kinase Cdk5 controls multiple aspects of axon patterning in vivo. Curr Biol 10, 599-602.

Cruz, J. C, Tseng, H. C, Goldman, J. A., Shih, H. and Tsai, L. H. (2003). Aberrant Cdk5 activation by p25 triggers pathological events leading to neurodegeneration and neurofibrillary tangles. Neuron 40, 471-483.

Hartmann, R. E., Yukitoshi, I., Kelly, R. B., Steven, M. P., David, F. W. and David, M. H. (2005). Treatment with an Amyloid-{beta} Antibody Ameliorates Plaque Load, Learning Deficits, and Hippocampal Long-Term Potentiation in a Mouse Model of Alzheimer's Disease. J Neurosci 25, 6213-6220.

Hock, et al. (2003). Antibodies against beta-amyloid slow cognitive decline in Alzheimer's disease. Neuron 38, 547-554.

Kitani, K., Oguma, S., Nishiki, T., Ohmori, I., Galons, H., Matsui, H., Meijer, L. and Tomizawa, K. (2007). A Cdk5 inhibitor enhances the induction of insulin secretion by exendin-4 both in vitro and in vivo. J Physiol Sci 57, 235-239.

Lai, K. O. and Ip, N. Y. (2009). Recent advances in understanding the roles of Cdk5 in synaptic plasticity. Biochim Biophys Acta 1792, 741-5.

Leclerc, S., Garnier, M., Hoessel, R., Marko, D., Bibb, J. A., Snyder, G. L., Greengard, P., Biernat, J., Wu, Y. Z. and Mandelkow, E. M. (2001). Indirubins inhibit glycogen synthase kinase-3 beta and CDK5/p25, two protein kinases involved in abnormal tau phosphorylation in Alzheimer's disease. A property common to most cyclin-dependent kinase inhibitors? J Biol Chem 276, 251-260.

Lin, H., Chen, M. C, Chiu, C. Y., Song, Y. M. and Lin, S. Y. (2007). Cdk5 regulates STAT3 activation and cell proliferation in medullary thyroid carcinoma cells. J Biol Chem 282, 2776-2784.

Malumbres, M. and Barbacid, M. (2009). Cell cycle, CDKs and cancer: a changing paradigm. Nat Rev Cancer. 9, 153-66.

Meijer, L., Borgne, A., Mulner, O., Chong, J. P., Blow, J. J., Inagaki, N., Inagaki, M., Delcros, J. G. and Moulinoux, J. P. (1997). Biochemical and cellular effects of roscovitine, a potent and selective inhibitor of the cyclin-dependent kinases cdc2, cdk2 and Cdk5. Eur J Biochem 243, 527-536.

Monaco, E. A. 3rd. (2004). Recent evidence regarding a role for Cdk5 dysregulation in Alzheimer's disease. Curr Alzheimer Res 1, 33-38.

Muntane, G., Dalfo, E., Martinez, A. and Ferrer, I. (2008). Phosphorylation of tau and alpha-synuclein in synaptic-enriched fractions of the frontal cortex in Alzheimer's disease, and in Parkinson's disease and related alpha-synucleinopathies. Neuroscience 152, 913-923.

Pareek, T. K., Keller, J., Kesavapany, S., Agarwal, N., Kuner, R., Pant, H. C., Iadarola, M. J., Brady, R. O. and Kulkarni, A. B. (2007). Cyclin-dependent kinase 5 modulates nociceptive signaling through direct phosphorylation of transient receptor potential vanilloid 1. Proc. Natl. Acad. Sci. U.S.A. 104, 660-665.

Pareek, T. K. and Kulkarni, A. B. (2006). Cdk5: a new player in pain signaling. Cell Cycle 5, 585-588.

Pareek, T. K., Keller, J., Kesavapany, S., Pant, H. C, Iadarola, M. J., Brady, R. O., Kulkarni, A. B. (2006). Cyclin-dependent kinase 5 activity regulates pain signaling. Proc. Natl. Acad. Sci. U.S.A. 103, 791-796.

Patrick, G. N., Zukerberg, L., Nikolic, M, de la Monte, S., Dikkes, P. and Tsai, L. H. (1999). Conversion of p35 to p25 deregulates Cdk5 activity and promotes neurodegeneration. Nature 402, 615-622.

Qu, D., Rashidian, J., Mount, M. P, Aleyasin, H., Parsanejad, M., Lira, A., Hague, E., Zhang, Y., Callaghan, S., Daigle, M., Rousseaux, M. W., Slack, R. S., Albert, P R., Vincent, I., Woulfe, J. M. and Park, D. S. (2007). Role of Cdk5-mediated phosphorylation of Prx2 in MPTP toxicity and Parkinson's disease. Neuron 55, 37-52.

Shapiro, G. I. (2006). Cyclin-dependent kinase pathways as targets for cancer treatment. J Clin. Oncol. 24, 1770-83.

Smith, P. D., Crocker, S. J., Jackson-Lewis, V., Jordan-Sciutto, K. L., Hayley, S., Mount, M. P., O'Hare, M. J., Callaghan, S., Slack, R. S., Przedborski, S., et al. (2003). Cyclin-dependent kinase 5 is a mediator of dopaminergic neuron loss in a mouse model of Parkinson's disease. Proc Natl Acad Sci USA 100, 13650-13655.

Strock, C. J., Park, J. I., Nakakura, E. K., Bova, G. S., Isaacs, J. T., Ball, D. W. and Nelkin, B. D. (2006). Cyclin-dependent kinase 5 activity controls cell motility and metastatic potential of prostate cancer cells. Cancer Res 66, 7509-7515.

Tsai, L. H., Takahashi, T, Caviness, V. S., Jr. and Harlow, E. (1993). Activity and expression pattern of cyclin-dependent kinase 5 in the embryonic mouse nervous system. Development 119, 1029-1040.

Ubeda, M., Rukstalis, J. M. and Habener, J. F. (2006). Inhibition of cyclin-dependent kinase 5 activity protects pancreatic beta cells from glucotoxicity. J Biol Chem 281, 28858-28864.

Wei, F. Y., Nagashima, K., Ohshima, T., Saheki, Y., Lu, Y. F., Matsushita, M., Yamada, Y., Mikoshiba, K., Seino, Y., Matsui H. and Tomizawa, K. (2005). Cdk5-dependent regulation of glucose-stimulated insulin secretion. Nat Med 11, 1104-1108.

Wang, J., Liu, S., Fu, Y., Wang, J. H. and Lu, Y. (2003). Cdk5 activation induces hippocampal CA1 cell death by directly phosphorylating NMDA receptors. Nat Neurosci 6, 1039-1047.

Wang, Y. (2008). The functional regulation of TRPV1 and its role in pain sensitization. Neurochem Res 33, 2008-2012.

Wei, F. Y. and Tomizawa, K. (2007). Cycline-dependent kinase 5 (Cdk5): a potential therapeutic target for the treatment of neurodegenerative diseases and diabetes mellitus. Mini Rev Med Chem 7, 1070-1074.

Xie, Z., Sanada, K., Samuels, B. A., Shih, H. and Tsai, L. H. (2003). Serine 732 phosphorylation of FAK by Cdk5 is important for microtubule organization, nuclear movement, and neuronal migration. Cell 114, 469-482.

Zheng, M., Leung, C. L. and Liem, R. K. (1998). Region-specific expression of cyclin-dependent kinase 5 (cdk5) and its activators, p35 and p39, in the developing and adult rat central nervous system. J Neurobiol 35, 141-159.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of inhibiting Cdk5 enzyme in human cells, the method comprising contacting said Cdk5 enzyme with an effective amount of a compound of Formula II:

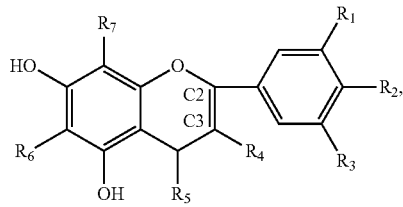

wherein
$R_1$, $R_2$ and $R_3$ are independently H, OH or $OCH_3$;
wherein $R_4$ is OH or $OR_{12}$, wherein $R_{12}$ is glucose,

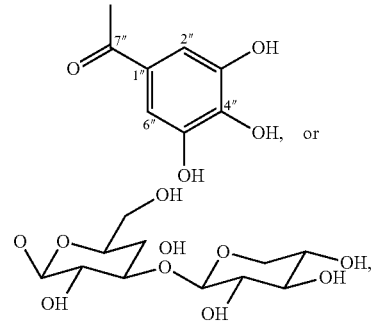

with the proviso that when $R_{12}$ is

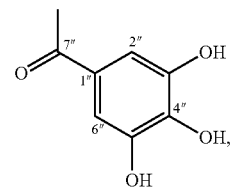

the bond between C2 and C3 indicated in Formula II is a single bond;
$R_5$ is H or =O;
$R_6$ is H; and
$R_7$ is OH, hydrogen, O-xylose, O-rhamnose or O-glucose.

2. The method of claim 1, wherein said compound is selected from the group consisting of:

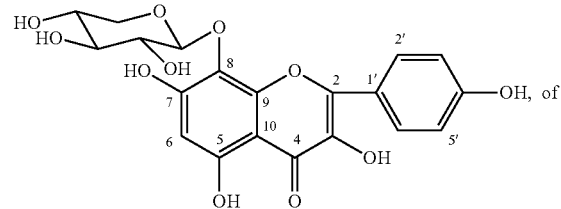

-continued

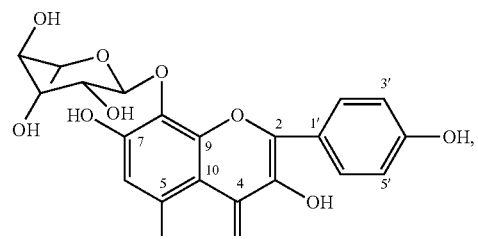
(F199-C16)

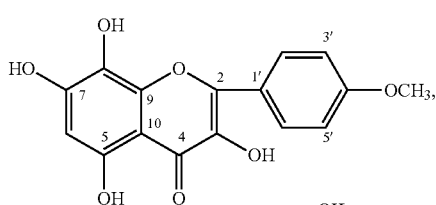
(F199-C23)

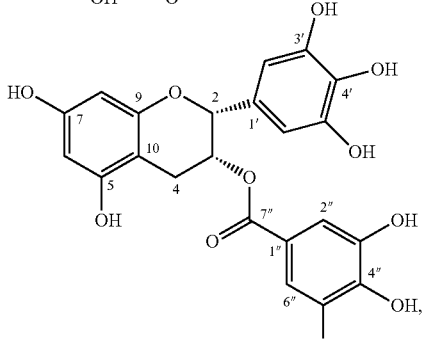
(F199-C35)

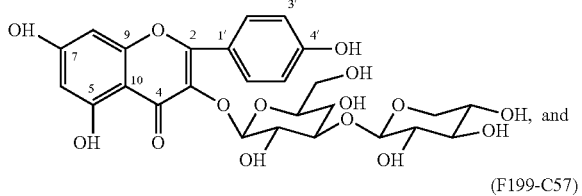
(F199-C42)

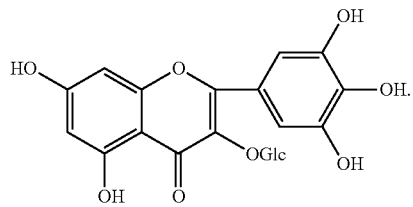
(F199-C57)

3. The method of claim 1, wherein R7 is OH or O-glucose.

4. A method of treating a disease in a subject, wherein the disease is associated with hyperactive Cdk5, the method comprising administering to the subject a pharmaceutically effective amount of a compound of Formula II:

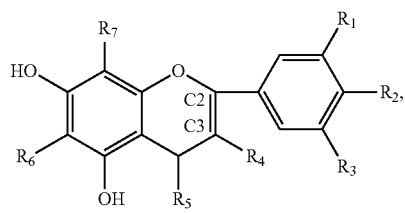

wherein
$R_1$, $R_2$ and $R_3$ are independently H, OH or $OCH_3$;
wherein $R_4$ is OH or $OR_{12}$, wherein $R_{12}$ is glucose,

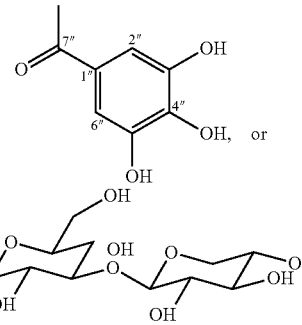

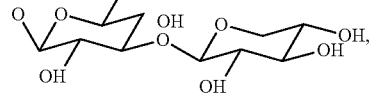

with the proviso that when $R_{12}$ is

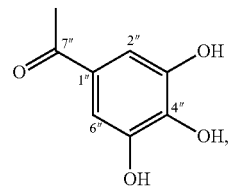

the bond between C2 and C3 indicated in Formula II is a single bond;
$R_5$ is H or =O;
$R_6$ is H; and
$R_7$ is OH, hydrogen, O-xylose, O-rhamnose or O-glucose;
and wherein the pharmaceutically effective amount of the compound produces a concentration within the ranges of 0.5 μM to 200 μM in the subject.

5. The method of claim 4, wherein said disease or disorder is neuropathic pain, stroke, brain trauma, epilepsy or neurodegenerative diseases.

6. The method of claim 5, wherein said neurodegenerative diseases is amyotrophic lateral sclerosis, Alzheimer's disease, Parkinson's disease or Huntington's disease.

7. The method of claim 4, wherein the effective amount produces the concentration within the range of 0.5 μM to 4 μM in the subject.

8. The method of claim 4, wherein the effective amount produces the concentration within the range of 3 μM to 50 μM in the subject.

9. The method of claim 4, wherein the effective amount produces the concentration within the range of 20 μM to 200 μM in the subject.

10. The method of claim 4, wherein said compound is selected from the group consisting of:

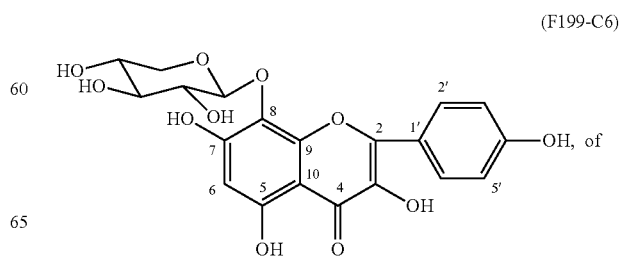
(F199-C6)

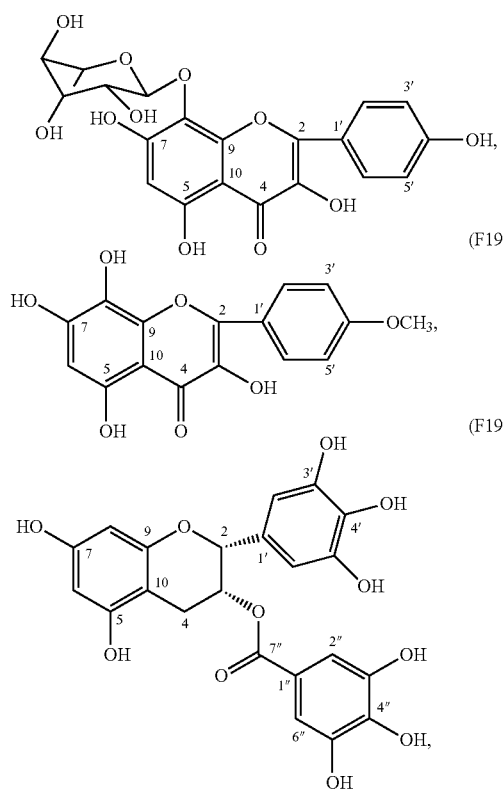
(F199-C16)
(F199-C23)
(F199-C35)
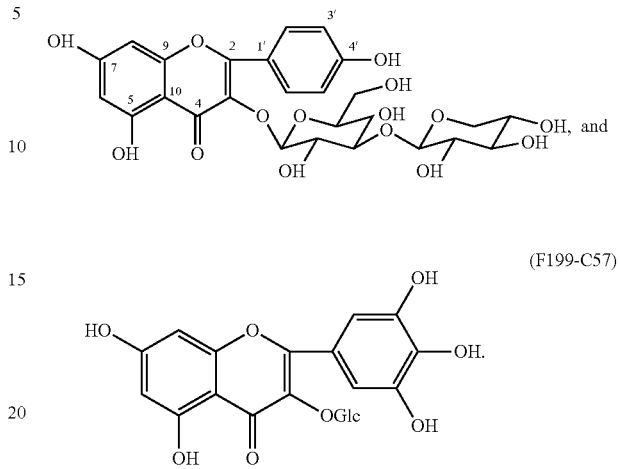
(F199-C42)
(F199-C57)
11. The method of claim 10, wherein the disease is neuropathic pain, stroke, brain trauma, epilepsy, or a neurodegenerative disease.
12. The method of claim 11, wherein said neurodegenerative disease is amyotrophic lateral sclerosis, Alzheimer's disease, Parkinson's disease, or Huntington's disease.
* * * * *